United States Patent
Lu et al.

(10) Patent No.: US 11,725,020 B2
(45) Date of Patent: *Aug. 15, 2023

(54) PRODRUGS OF A CDK INHIBITOR FOR TREATING CANCERS

(71) Applicants: RISEN (SUZHOU) PHARMA TECH CO., LTD., Jiangsu (CN); SHANGHAI JUNSHI BIOSCIENCES CO., LTD., Shanghai (CN)

(72) Inventors: Jiasheng Lu, Shanghai (CN); Jiamin Gu, Suzhou (CN); Gang Chen, Suzhou (CN); Xiaolin Zhang, Suzhou (CN); Feng Zhou, Suzhou (CN); Xianqi Kong, Dollard des-Ormeaux (CA)

(73) Assignees: RISEN (SUZHOU) PHARMA TECH CO., LTD., Suzhou (CN); SHANGHAI JUNSHl BIOSCIENCES CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/548,899

(22) Filed: Dec. 13, 2021

(65) Prior Publication Data

US 2022/0204541 A1 Jun. 30, 2022

Related U.S. Application Data

(63) Continuation of application No. 16/856,603, filed on Apr. 23, 2020, now Pat. No. 11,225,497.

(30) Foreign Application Priority Data

Apr. 26, 2019 (CN) .......................... 201910343182.5

(51) Int. Cl.
| | |
|---|---|
| *C07F 9/6574* | (2006.01) |
| *C07D 401/14* | (2006.01) |
| *C07D 401/12* | (2006.01) |
| *C07F 9/22* | (2006.01) |
| *A61K 9/00* | (2006.01) |

(52) U.S. Cl.
CPC ........ *C07F 9/65744* (2013.01); *C07D 401/12* (2013.01); *C07D 401/14* (2013.01); *C07F 9/222* (2013.01); *A61K 9/0019* (2013.01); *A61K 9/0053* (2013.01)

(58) Field of Classification Search
None
See application file for complete search history.

(56) References Cited

U.S. PATENT DOCUMENTS

| 11,225,497 B2 * | 1/2022 | Lu .................. C07D 401/12 |
| 2008/0139620 A1 | 6/2008 | Wyatt |
| 2009/0318430 A1 | 12/2009 | Pike et al. |

FOREIGN PATENT DOCUMENTS

| WO | 2006077414 A1 | 7/2006 |
| WO | 2006077416 A1 | 7/2006 |
| WO | 2006077419 A1 | 7/2006 |
| WO | 2020005807 A1 | 1/2020 |

OTHER PUBLICATIONS

Santo et al., AT7519, A novel small molecule multi-cyclin-dependent kinase inhibitor, induces apoptosis in multiple myeloma via GSK-3B activation and RNA polymerase II inhibition, Oncogene, 2010, vol. 29, pp. 2325-2336.

* cited by examiner

*Primary Examiner* — Joseph R Kosack
(74) *Attorney, Agent, or Firm* — BCF LLP

(57) ABSTRACT

There are provided compounds of Formula I, and pharmaceutically acceptable salts and esters thereof, and pharmaceutical compositions thereof, used for inhibition or modulation of the activity of cyclin dependent kinases (CDK) and/or glycogen synthase kinase-3 (GSK-3), for the treatment of disease states or conditions mediated by cyclin dependent kinases and/or glycogen synthase kinase-3, including cancers.

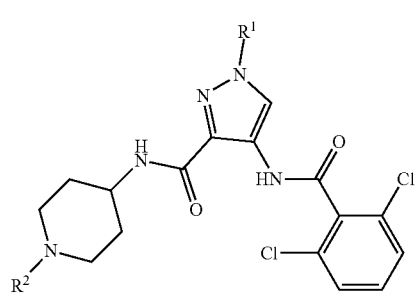

(I)

20 Claims, 3 Drawing Sheets

PRODRUGS OF A CDK INHIBITOR FOR TREATING CANCERS

CROSS-REFERENCE TO RELATED APPLICATIONS

This application is a Continuation of U.S. application Ser. No. 16/856,603 filed Apr. 23, 2020, now U.S. Pat. No. 11,225,497, which claims the benefit of priority to Chinese application no. 201910343182.5 filed Apr. 26, 2019, the entire contents of which are hereby incorporated by reference.

FIELD

The present disclosure relates to derivatives and prodrugs of 4-(2,6-dichlorobenzamido)-N-(4-piperidinyl)-1H-pyrazole-3-carboxamide and compositions thereof that inhibit or modulate the activity of cyclin dependent kinases (CDK) and/or glycogen synthase kinase-3 (GSK-3), and treat disease states or conditions mediated by cyclin dependent kinases and/or glycogen synthase kinase-3, such as cancers.

BACKGROUND 4-(2,6-Dichlorobenzamido)-N-(4-piperidinyl)-1H-pyrazole-3-carboxamide (a pyrazole derivative, also named as 4-[(2,6-dichlorobenzoyl)amino]-N-4-piperidinyl-1H-pyrazole-3-carboxamide, 4-(2,6-Dichlorobenzoylamino)-1H-pyrazole-3-carboxylic acid N-(piperidin-4-yl)amide, AT7519, AT-7519, or AT7519M) was reported as early as year 2006 by Berdini and co-workers (see, for example, WO2005012256), with the following chemical structure:

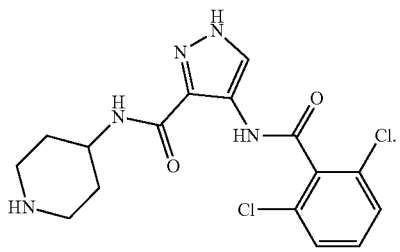 [SMILES: O=C(NC1CCNCC1)c1n[nH]cc1NC(=O)c1c(Cl)cccc1Cl]

AT7519 is an orally bioavailable small molecule with potential antineoplastic activity. It selectively binds to and inhibits cyclin dependent kinases (CDKs), which may result in cell cycle arrest, induction of apoptosis, and inhibition of tumor cell proliferation. CDKs are serine/theronine kinases involved in regulation of the cell cycle and may be overexpressed in some types of cancer cells. To date, the compound has appeared in over 100 publications, including patents/patent applications, and scientific journal papers and communications. Examples of patents and early patent applications include WO 2006077425, WO 2006077416, WO 2006077419, U.S. Pat. No. 7,385,059, and US2010021420. Examples of scientific papers include "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design" (Wyatt, et al., *J. Med. Chem.*, 2008, 51(16), 4986-4999), "Biological characterization of AT7519, a small-molecule inhibitor of cyclin-dependent kinases, in human tumor cell lines" (Squires, et al., *Mol. Cancer Ther.*, 2009, 8(2), 324-332), "AT7519, a Cyclin-Dependent Kinase Inhibitor, Exerts Its Effects by Transcriptional Inhibition in Leukemia Cell Lines and Patient Samples" (Squires, et al., *Mol. Cancer Ther.*, 2010, 9(4), 920-928), and "AT7519, A novel small molecule multi-cyclin-dependent kinase inhibitor, induces apoptosis in multiple myeloma via GSK-3β activation and RNA polymerase II inhibition" (Santo, et al., *Oncogene*, 2010, 29(16), 2325-2336).

Many studies have demonstrated potential therapeutic use of AT7519 in treating cancers. AT7519 is an ATP competitive CDK inhibitor with a $K_i$ value of 38 nM for CDK1. AT7519 is inactive against all non-CDK kinases with the exception of GSK3β (IC50=89 nM). AT7519 shows potent antiproliferative activity in a variety of human tumor cell lines with IC50 values ranging from 40 nM for MCF-7 to 940 nM for SW620 consistent with the inhibition of CDK1 and CDK2 (Squires M S, et al. *Mol. Cancer Ther,* 2009, 8(2), 324-332). AT7519 induces dose-dependent cytotoxicity in multiple myeloma (MM) cell lines with IC50 values ranging from 0.5 to 2 μM at 48 hours, with the most sensitive cell lines being MM.1S (0.5 μM) and U266 (0.5 μM) and the most resistant MM.1R (>2 μM). It does not induce cytotoxicity in peripheral blood mononuclear cells (PBMNC). AT7519 partially overcomes the proliferative advantage conferred by IL6 and IGF-1 as well as the protective effect of bone marrow stromal cells (BMSCs). AT7519 induces rapid dephosphorylation of RNA pol II CTD at serine 2 and serine 5 sites, and leads to the inhibition of transcription, partially contributing to AT7519 induced cytotoxicity of MM cells. AT7519 also induces activation of GSK-3β by down-regulating GSK-3β phosphorylation, which may contribute to AT7519 induced apoptosis independent of the inhibition of transcription (Santo L, et al. *Oncogene,* 2010, 29(16), 2325-2336).

A twice daily dosing of AT7519 (9.1 mg/kg) has been shown to cause tumor regression of both early-stage and advanced-stage s.c. tumors in the HCT116 and HT29 colon cancer xenograft models (Squires M S, et al. *Mol. Cancer Ther,* 2009, 8(2), 324-332). AT7519 treatment (15 mg/kg) can inhibit tumor growth and prolong the median overall survival of mice in the human MM xenograft mouse model in association with increased caspase 3 activation (Santo L, et al. *Oncogene,* 2010, 29(16), 2325-2336).

AT7519 has been considered a potential therapeutic for a variety of indications including multiple myeloma, mantle cell lymphoma, chronic lymphocytic leukemia, solid tumor, non-Hodgkin lymphoma, and hematological neoplasm. Several clinical trials to test AT-7519 in the treatment of multiple myeloma (MM), chronic lymphocytic leukemia (CLL), and solid tumors including mantle cell lymphoma (MCL) have also been initiated (see for example, "A Phase I study of cyclin-dependent kinase inhibitor, AT7519, in patients with advanced cancer: NCIC Clinical Trials Group IND 177" (Chen, E. X., et al., *Br. J. of Cancer,* 2014, 111(12), 2262-2267)). However, because of the involvement of AT7519 in multiple pathways essential for transcription and proliferation, the potential for adverse events is high. Indeed, AT7519 has shown a significant level of toxicity in both animal and human testing. The majority of patients treated with AT7519 had at least one treatment-related AE (82.1%). The majority of AEs were Common Terminology Criteria for Adverse Events grade 1 or 2 in severity (46.7% and 37.8%, respectively). The most common treatment-emergent AEs were nausea (50.0%), fatigue (42.9%), vomiting and anorexia (39.3% each), constipation (32.1%) and peripheral edema, pyrexia and hypotension (25.0% each) (Mahadevan, D; et al., *Ann. Oncol.*, 2011, 22:2137-2143). In a phase I clinical trial, AT7519M dose was escalated to 32.4 mg/m². Among the initial three patients enrolled, one patient experienced DLT (grade 3 fatigue). Two additional patients were enrolled at this dose level, both of whom experienced DLTs (febrile neutropenia and grade 3 hypokalemia and mucositis) (Chen, E. X.; et al., *Br. J. Cancer*, 2014, 111:2262-2267).

It would be desirable to enhance potency and/or reduce toxicity of AT7519 for therapeutic use.

SUMMARY

It is an object of the present invention to ameliorate at least some of the deficiencies present in the prior art. Embodiments of the present technology have been developed based at least in part on the inventors' appreciation that there is a need for reducing the toxicity of 4-(2,6-dichlorobenzamido)-N-(4-piperidinyl)-1H-pyrazole-3-carboxamide (AT7519) for its use in therapeutic applications. These and other needs can be satisfied by the disclosure herein of AT7519 derivatives and/or prodrugs, pharmaceutical compositions and uses thereof to inhibit or modulate the activity of a cyclin dependent kinase (CDK) and/or glycogen synthase kinase-3 (GSK-3), and treat disease states or conditions mediated by cyclin dependent kinases and/or glycogen synthase kinase-3, such as cancers.

In a first aspect, there are provided compounds of Formula I, or pharmaceutically acceptable salts or esters thereof:

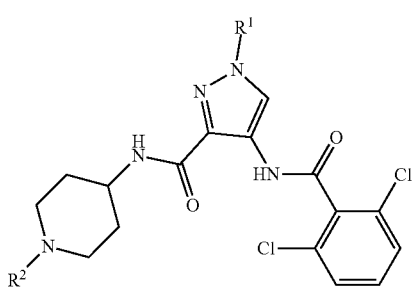

(I)

where $R^1$ and $R^2$ are independently a hydrogen (H) or a protecting group (P), and the protecting groups are the same or different, provided at least one of $R^1$ and $R^2$ is not a hydrogen.

In one embodiment $R^1$ and $R^2$ are both independently a protecting group selected from: acyl, carbonyl, thiocarbonyl, and carbamoyl groups; substituted or unsubstituted acetyl, aminoalkanoyl, and α-aminoalkanoyl; substituted or unsubstituted acyl groups derived from a natural or unnatural amino acid; substituted or unsubstituted acyl groups of peptide residues; substituted or unsubstituted cycloalkane-carbonyl, heterocycloalkane-carbonyl, alkoxycarbonyl, aryloxycarbonyl, heteroalkoxycarbonyl, or heteroaryloxycarbonyl; and O-substituted hydroxymethyl group. In an embodiment, $R^1$ and $R^2$ are the same protecting group. In another embodiment, $R^1$ and $R^2$ are different protecting groups.

In another embodiment, $R^1$ and $R^2$ are independently a hydrogen or a protecting group having the structure $R^3W(R^4R^5C)_m$—, where: m is an integer selected from 1 to 6; W is oxygen (—O—), sulfur (—S—), nitrogen (—NH—), or absent; $R^4$ and $R^5$ are independently hydrogen or lower alkyl group; and $R^3$ is

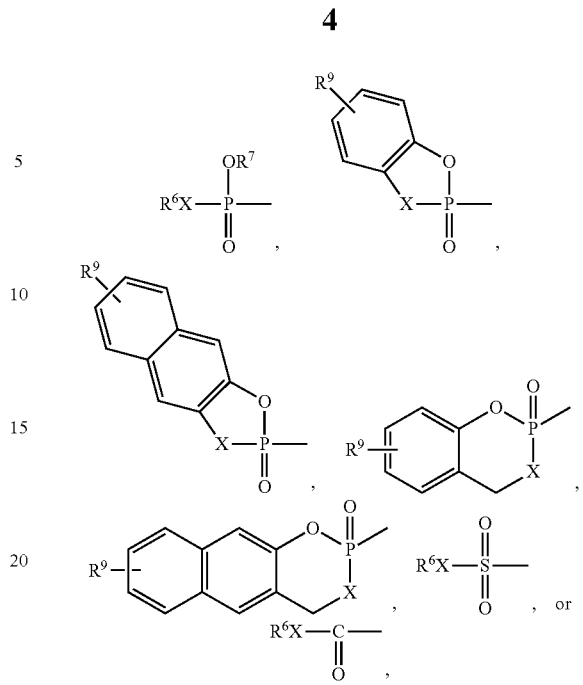

where:
X is oxygen (—O—), sulfur (—S—), nitrogen (—NH—), or a methylene (—CH₂—) group;

$R^6$ and $R^7$ are independently a hydrogen; a substituted or unsubstituted alkyl or cycloalkyl; an aryl or heteroaryl group without or with substitution; a PEG moiety having the structure $R^8$—(OCH₂CH₂)ₙ—, where n=1 to 10, and $R^8$ is a hydrogen or a lower alkyl; an ester-forming group such as a lower alkyl or an aryl group; or a salt-forming moiety when X is oxygen or sulfur, such as a sodium, a potassium, a tetraethylammonium, or a tetrabutylammonium; or the combination of $R^6$ and X is an alky or aryl group with or without further substitution; provided at least one of $R^1$ and $R^2$ is not a hydrogen.

In a further embodiment, $R^2$ is a hydrogen, $R^1$ is a protecting group selected from acyl, carbonyl, thiocarbonyl, and carbamoyl groups; substituted or unsubstituted acetyl, aminoalkanoyl, and α-aminoalkanoyl; acyl groups derived from a natural or unnatural amino acid with or without substitution; acyl groups of peptide residues; substituted or unsubstituted cycloalkane-carbonyl, heterocycloalkane-carbonyl, alkoxycarbonyl, aryloxycarbonyl, heteroalkoxycarbonyl, or heteroaryloxycarbonyl; O-substituted hydroxymethyl group with or without substituents; and $R^3W(R^4R^5C)_m$—, where m=0 to 6 and W, X, $R^3$, $R^4$, and $R^5$ are as defined above.

In another embodiment, $R^1$ is a hydrogen, and $R^2$ is $R^3W(R^4R^5C)_m$—, where m is an integer selected from 1 to 6, and W, X, $R^3$, $R^4$, and $R^5$ are as defined above.

In a further embodiment, $R^1$ and $R^2$ are independently selected from a hydrogen,

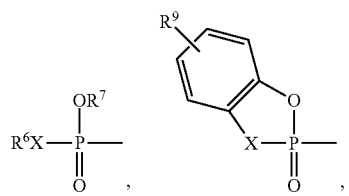

-continued

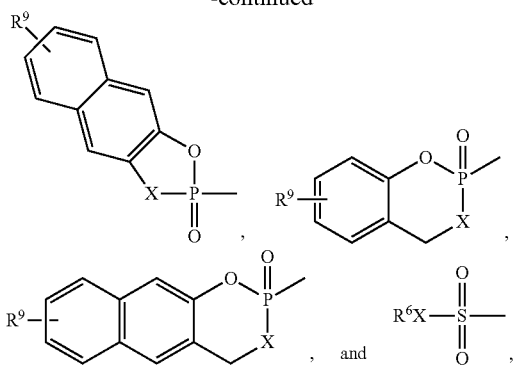

where X, $R^6$ and $R^7$ are as defined above and $R^9$ is a substituent group, provided that one of $R^1$ and $R^2$ is not a hydrogen. In some embodiments, $R^9$ is a substituent group selected from lower alkyl, hydroxyl, halogen (—F, —Cl, —Br, or —I), nitro, amino, lower alkyl amino, and lower alkyloxy group.

In some embodiments, the compound of Formula I is a compound shown in Table 1, or a pharmaceutically-acceptable salt, ester, chelate, hydrate, solvate, stereoisomer, or polymorphic form thereof.

In some embodiments, the compound of Formula I is a derivative or a prodrug of AT7519.

TABLE 1

Examples of compounds of Formula I.

| No. | Structure |
|---|---|
| 1 | 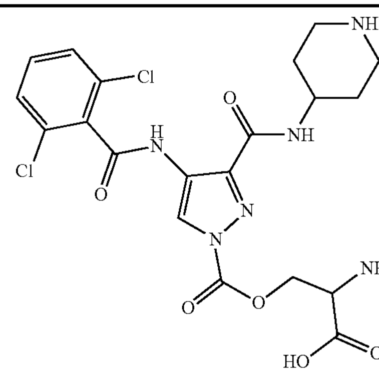 |
| 2 | 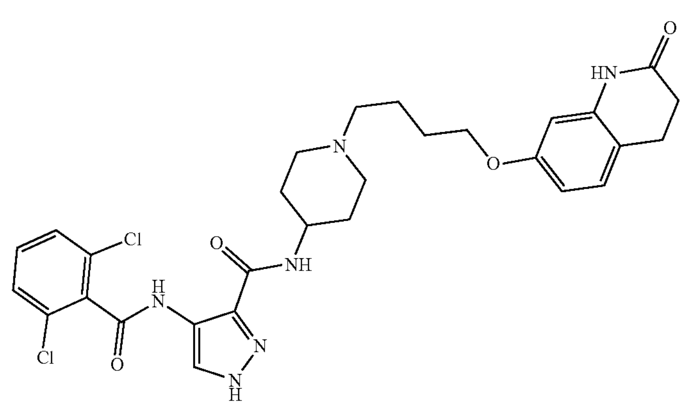 [SMILES: O=C1CCc2ccc(OCCCCN3CCC(NC(=O)c4n[nH]cc4NC(=O)c4c(Cl)cccc4Cl)CC3)cc2N1] |

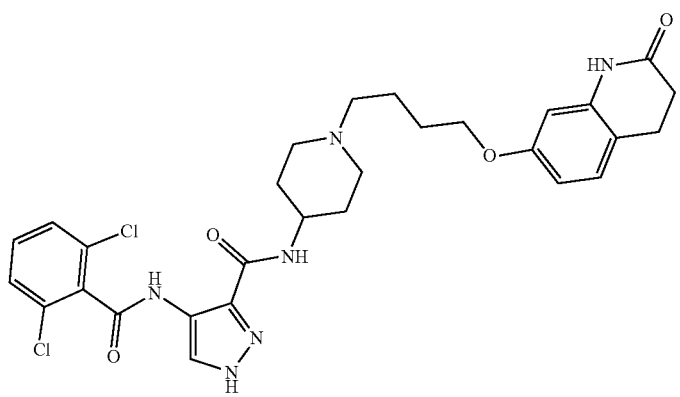

TABLE 1-continued
Examples of compounds of Formula I.
| No. | Structure |
|---|---|
| 3 | 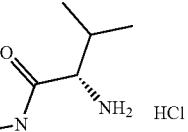 |
| 4 | 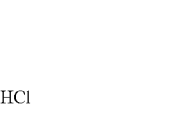 |
| 5 | 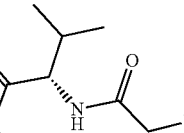 |
| 6 | 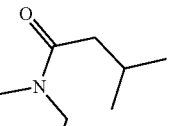 |

TABLE 1-continued

Examples of compounds of Formula I.

| No. | Structure |
|---|---|
| 7 | *(structure: 2,6-dichlorobenzamide-pyrazole-carboxamide-piperidine-glycyl-valine·HCl)* |
| 8 | *(structure: 2,6-dichlorobenzamide-pyrazole-carboxamide-N-Boc-piperidine, N1-lauroyl)* |
| 9 | *(structure: 2,6-dichlorobenzamide-pyrazole-carboxamide-N-Boc-piperidine, N1-Boc)* |

TABLE 1-continued
Examples of compounds of Formula I.
| No. | Structure |
|---|---|
| 10 | 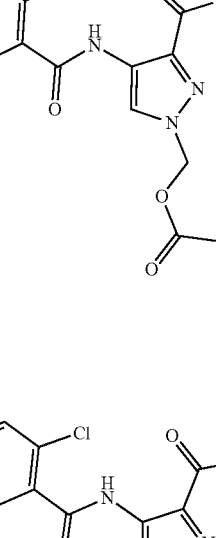 |
| 11 | 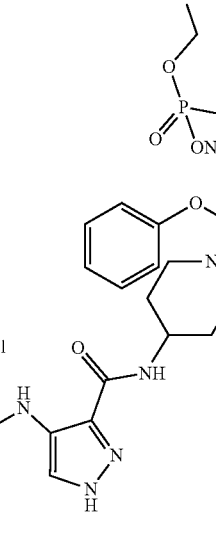 |
| 12 | 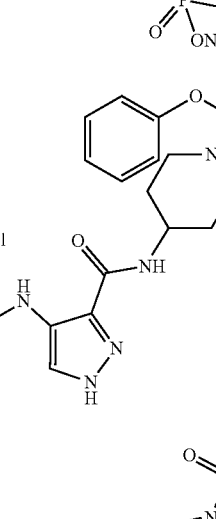 |
| 13 | 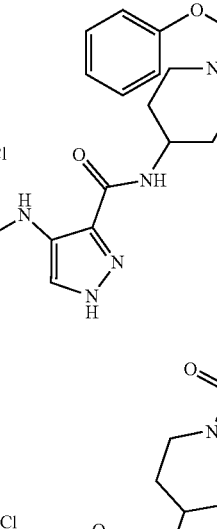 |

TABLE 1-continued
Examples of compounds of Formula I.
| No. | Structure |
|---|---|
| 14 | 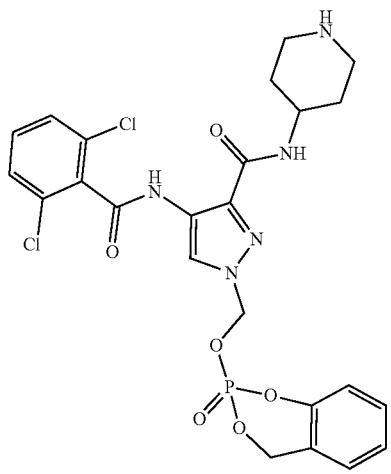 [SMILES: O=C(NC1CCNCC1)c1nn(COP2(=O)OCc3ccccc3O2)cc1NC(=O)c1c(Cl)cccc1Cl] |
| 15 | 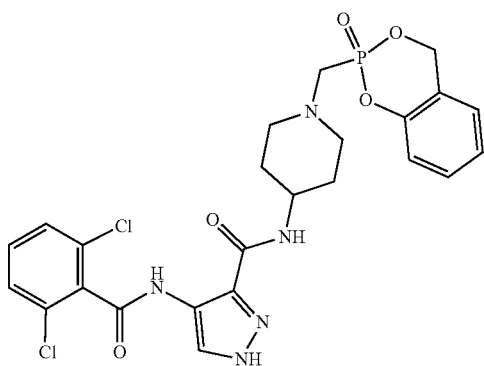 [SMILES: O=C(NC1CCN(CP2(=O)OCc3ccccc3O2)CC1)c1n[nH]cc1NC(=O)c1c(Cl)cccc1Cl] |
| 16 | 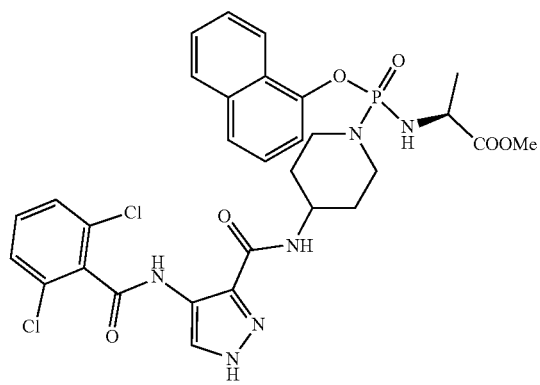 [SMILES: COC(=O)[C@H](C)NP(=O)(Oc1cccc2ccccc12)N1CCC(NC(=O)c2n[nH]cc2NC(=O)c2c(Cl)cccc2Cl)CC1] |

TABLE 1-continued
Examples of compounds of Formula I.
| No. | Structure |
|---|---|
| 17 | 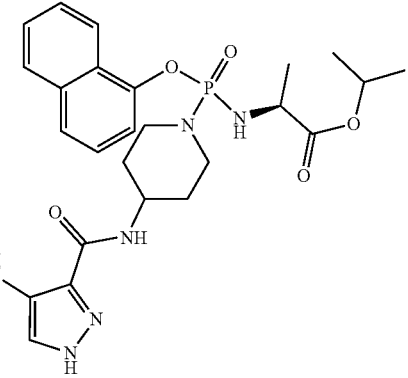 |
| 18 | 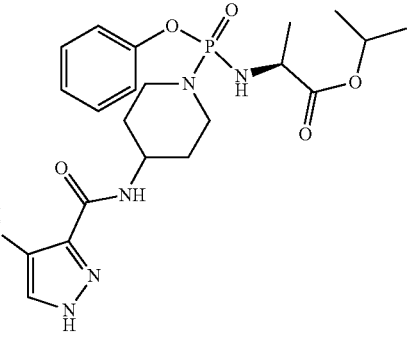 |
| 19 | 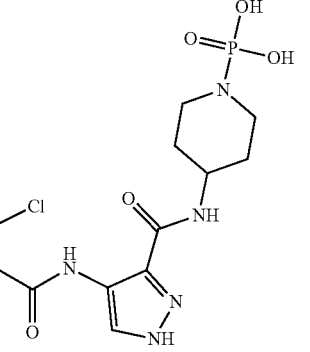 |
| 20 | 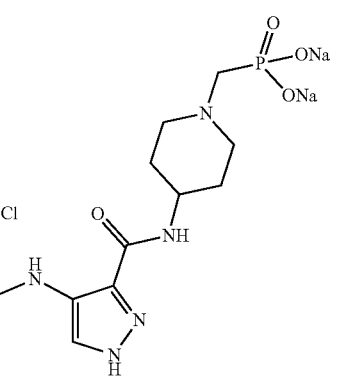 |

TABLE 1-continued
Examples of compounds of Formula I.
| No. | Structure |
|---|---|
| 21 | 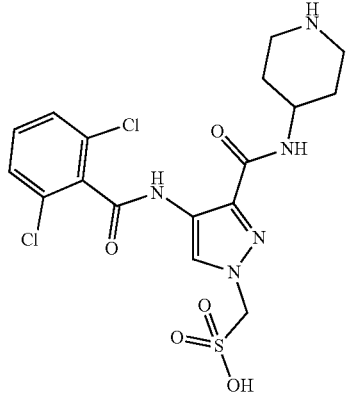 [SMILES: O=C(NC1CCNCC1)c1nn(CS(=O)(=O)O)cc1NC(=O)c1c(Cl)cccc1Cl] |
| 22 | 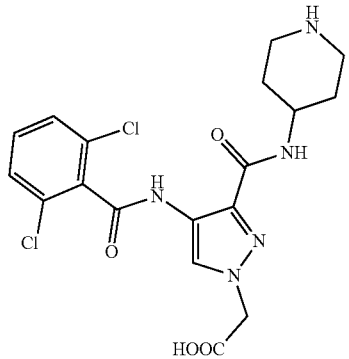 [SMILES: O=C(O)Cn1cc(NC(=O)c2c(Cl)cccc2Cl)c(C(=O)NC2CCNCC2)n1] |
| 23 | 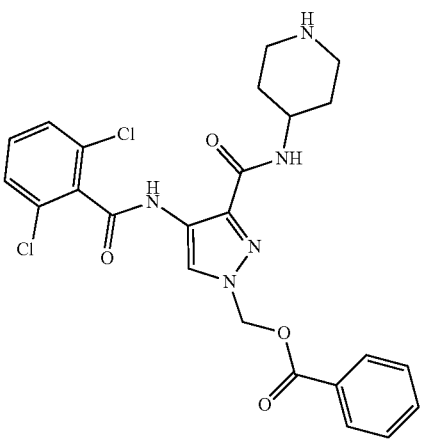 [SMILES: O=C(OCn1cc(NC(=O)c2c(Cl)cccc2Cl)c(C(=O)NC2CCNCC2)n1)c1ccccc1] |

TABLE 1-continued

Examples of compounds of Formula I.

| No. | Structure |
|---|---|
| 24 | 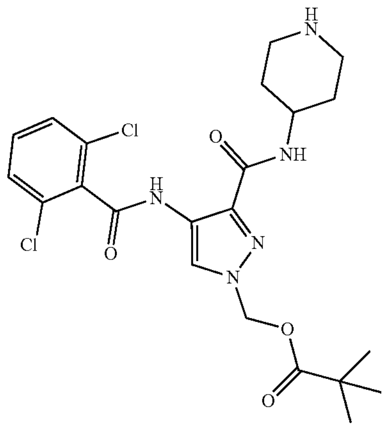 [SMILES: CC(C)(C)C(=O)OCn1cc(NC(=O)c2c(Cl)cccc2Cl)c(C(=O)NC2CCNCC2)n1] |
| 25 | 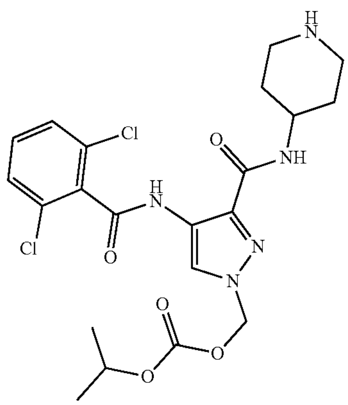 [SMILES: CC(C)OC(=O)OCn1cc(NC(=O)c2c(Cl)cccc2Cl)c(C(=O)NC2CCNCC2)n1] |
| 26 | 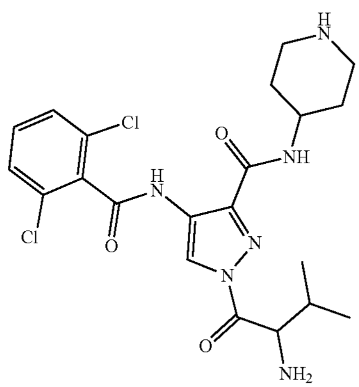 [SMILES: CC(C)C(N)C(=O)n1cc(NC(=O)c2c(Cl)cccc2Cl)c(C(=O)NC2CCNCC2)n1] |
| 27 | 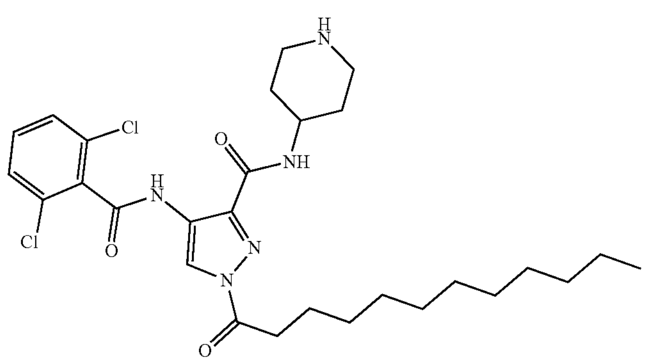 [SMILES: CCCCCCCCCCCC(=O)n1cc(NC(=O)c2c(Cl)cccc2Cl)c(C(=O)NC2CCNCC2)n1] |

US 11,725,020 B2
21                                                                         22
TABLE 1-continued
Examples of compounds of Formula I.
No.         Structure
28
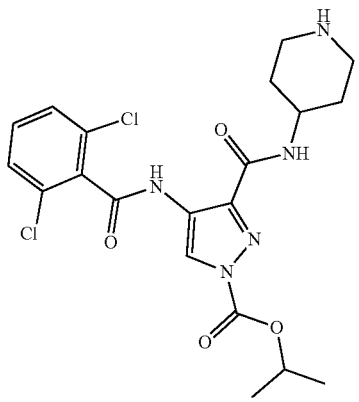 [SMILES: CC(C)OC(=O)n1cc(NC(=O)c2c(Cl)cccc2Cl)c(C(=O)NC2CCNCC2)n1]
29
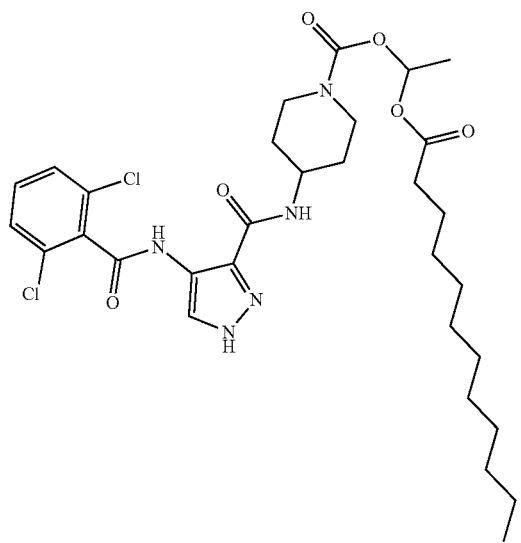 [SMILES: CCCCCCCCCCCC(=O)OC(C)OC(=O)N1CCC(NC(=O)c2n[nH]cc2NC(=O)c2c(Cl)cccc2Cl)CC1]
30
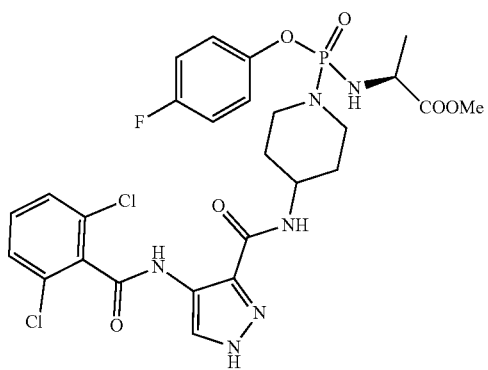 [SMILES: COC(=O)[C@H](C)NP(=O)(Oc1ccc(F)cc1)N1CCC(NC(=O)c2n[nH]cc2NC(=O)c2c(Cl)cccc2Cl)CC1]

TABLE 1-continued
Examples of compounds of Formula I.
| No. | Structure |
|---|---|
| 31 | 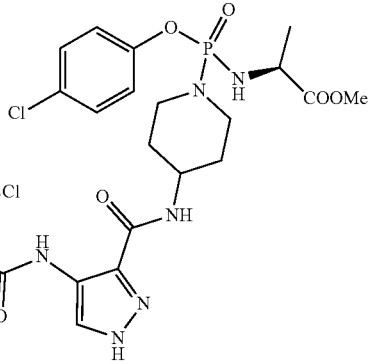 |
| 32 | 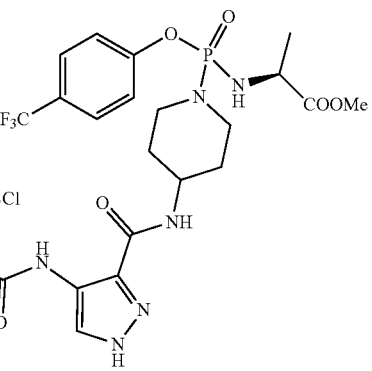 |
| 33 | 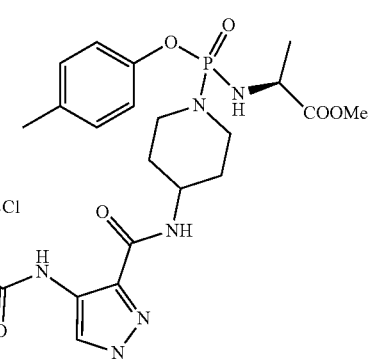 |
| 34 | 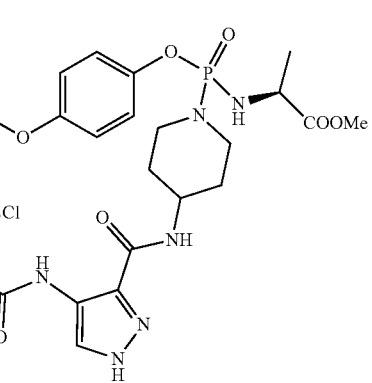 |

TABLE 1-continued

Examples of compounds of Formula I.

| No. | Structure |
|---|---|
| 35 | 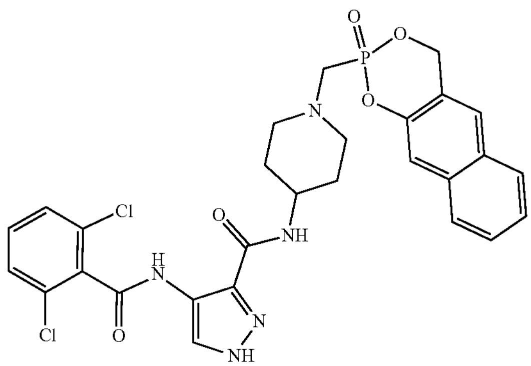 [SMILES: O=C(NC1CCN(CP2(=O)OCc3cc4ccccc4cc3O2)CC1)c1n[nH]cc1NC(=O)c1c(Cl)cccc1Cl] |
| 36 | 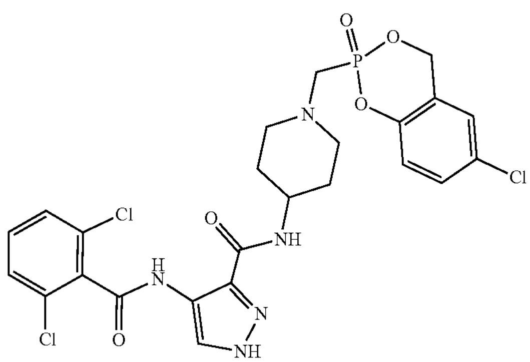 [SMILES: O=C(NC1CCN(CP2(=O)OCc3cc(Cl)ccc3O2)CC1)c1n[nH]cc1NC(=O)c1c(Cl)cccc1Cl] |
| 37 | 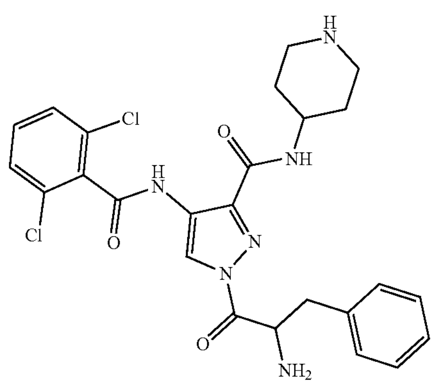 [SMILES: NC(Cc1ccccc1)C(=O)n1cc(NC(=O)c2c(Cl)cccc2Cl)c(C(=O)NC2CCNCC2)n1] |
| 38 | 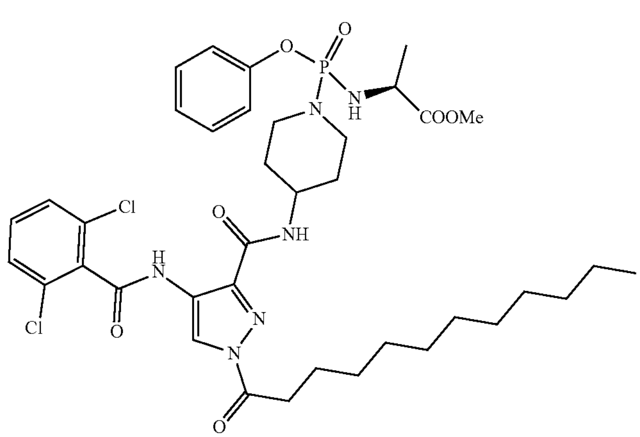 [SMILES: CCCCCCCCCCCC(=O)n1cc(NC(=O)c2c(Cl)cccc2Cl)c(C(=O)NC2CCN(P(=O)(N[C@@H](C)C(=O)OC)Oc3ccccc3)CC2)n1] |

27 28
TABLE 1-continued
Examples of compounds of Formula I.
| No. | Structure |
|---|---|
| 39 | 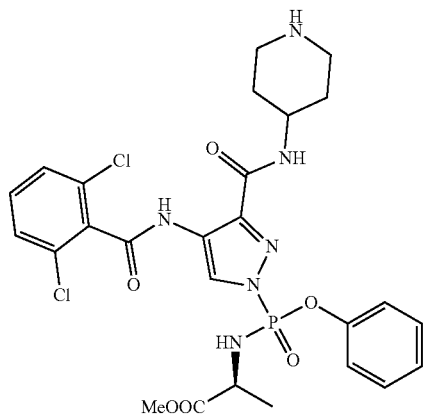 [SMILES: COC(=O)[C@H](C)NP(=O)(Oc1ccccc1)n1cc(NC(=O)c2c(Cl)cccc2Cl)c(C(=O)NC2CCNCC2)n1] |
| 40 | 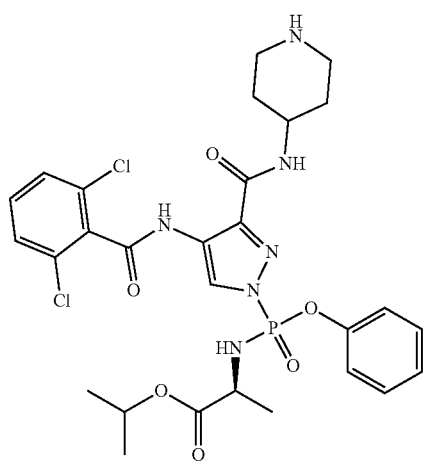 [SMILES: CC(C)OC(=O)[C@H](C)NP(=O)(Oc1ccccc1)n1cc(NC(=O)c2c(Cl)cccc2Cl)c(C(=O)NC2CCNCC2)n1] |
| 41 | 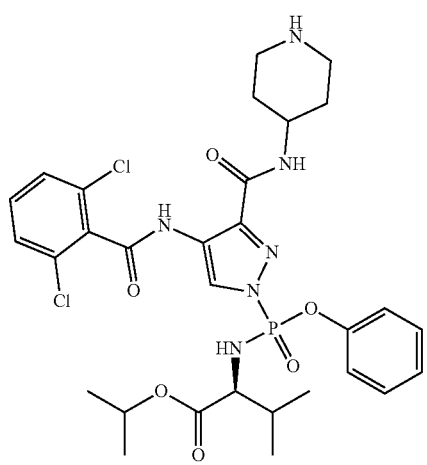 [SMILES: CC(C)OC(=O)[C@@H](NP(=O)(Oc1ccccc1)n1cc(NC(=O)c2c(Cl)cccc2Cl)c(C(=O)NC2CCNCC2)n1)C(C)C] |

TABLE 1-continued
Examples of compounds of Formula I.
| No. | Structure |
|---|---|
| 42 | 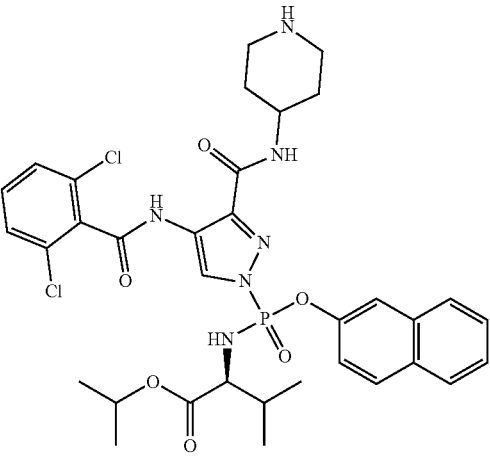 [SMILES: CC(C)OC(=O)[C@@H](NP(=O)(Oc1ccc2ccccc2c1)n1cc(NC(=O)c2c(Cl)cccc2Cl)c(C(=O)NC2CCNCC2)n1)C(C)C] |
| 43 | 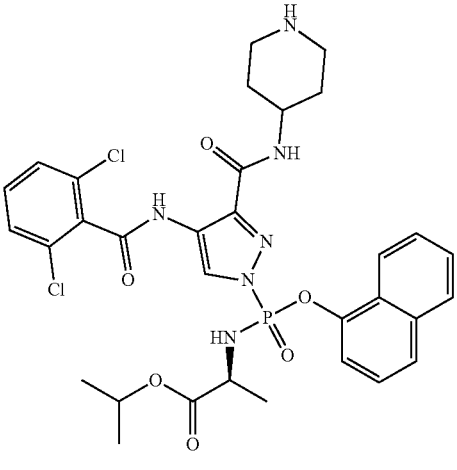 [SMILES: CC(C)OC(=O)[C@H](C)NP(=O)(Oc1cccc2ccccc12)n1cc(NC(=O)c2c(Cl)cccc2Cl)c(C(=O)NC2CCNCC2)n1] |
| 44 | 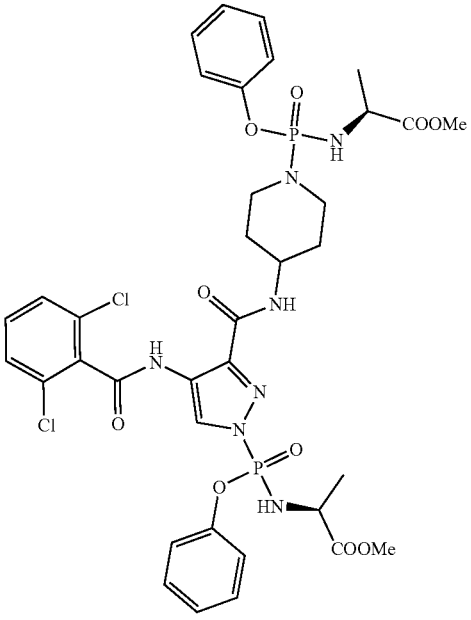 [SMILES: COC(=O)[C@H](C)NP(=O)(Oc1ccccc1)N1CCC(NC(=O)c2nn(P(=O)(N[C@@H](C)C(=O)OC)Oc3ccccc3)cc2NC(=O)c2c(Cl)cccc2Cl)CC1] |

TABLE 1-continued
Examples of compounds of Formula I.
| No. | Structure |
|---|---|
| 45 | 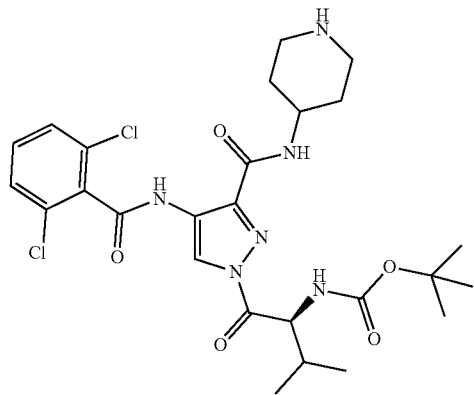 [SMILES: CC(C)[C@H](NC(=O)OC(C)(C)C)C(=O)n1cc(NC(=O)c2c(Cl)cccc2Cl)c(C(=O)NC2CCNCC2)n1] |
| 46 | 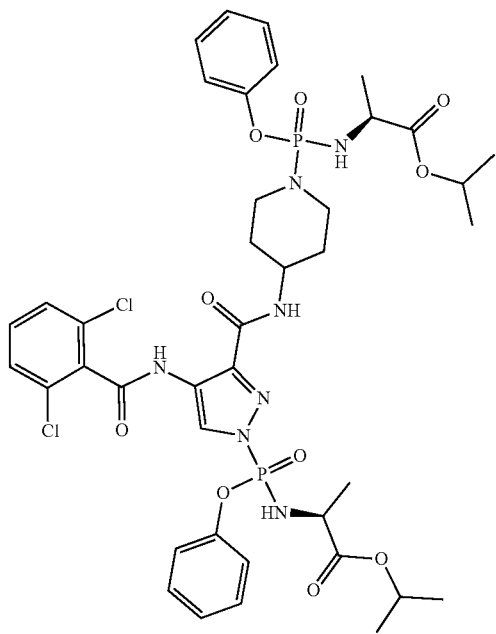 [SMILES: CC(C)OC(=O)[C@H](C)NP(=O)(Oc1ccccc1)N1CCC(NC(=O)c2nn(P(=O)(N[C@@H](C)C(=O)OC(C)C)Oc3ccccc3)cc2NC(=O)c2c(Cl)cccc2Cl)CC1] |

TABLE 1-continued
Examples of compounds of Formula I.
| No. | Structure |
|---|---|
| 47 | 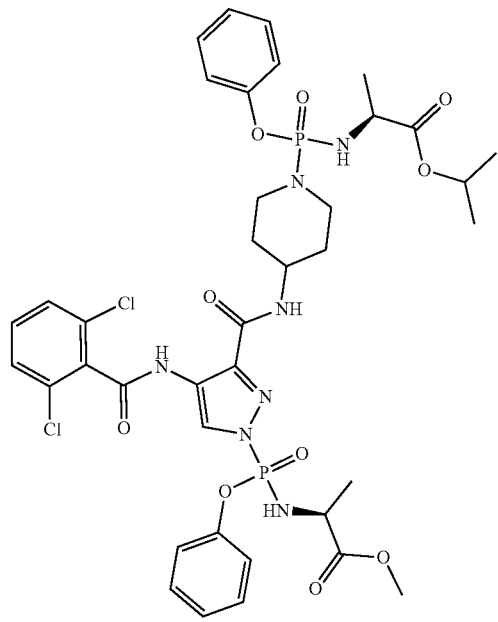 [SMILES: COC(=O)[C@H](C)NP(=O)(Oc1ccccc1)n1cc(NC(=O)c2c(Cl)cccc2Cl)c(C(=O)NC2CCN(P(=O)(N[C@@H](C)C(=O)OC(C)C)Oc3ccccc3)CC2)n1] |
| 48 | 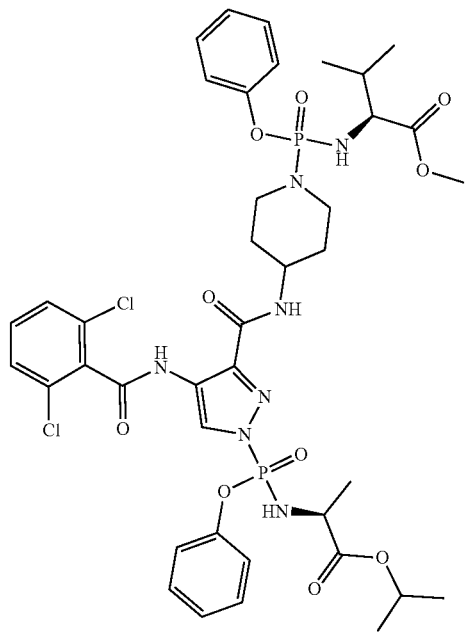 [SMILES: COC(=O)[C@@H](NP(=O)(Oc1ccccc1)N1CCC(NC(=O)c2nn(P(=O)(N[C@@H](C)C(=O)OC(C)C)Oc3ccccc3)cc2NC(=O)c2c(Cl)cccc2Cl)CC1)C(C)C] |

TABLE 1-continued
Examples of compounds of Formula I.
| No. | Structure |
|---|---|
| 49 | 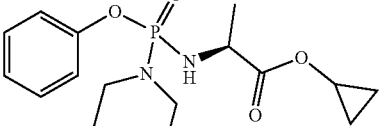 |
| 50 | 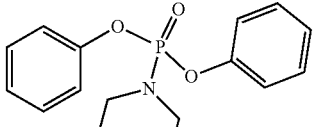 |
| 51 | 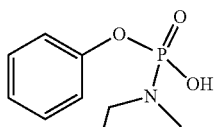 |
| 52 | 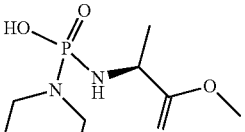 |

TABLE 1-continued
Examples of compounds of Formula I.
| No. | Structure |
|---|---|
| 53 | 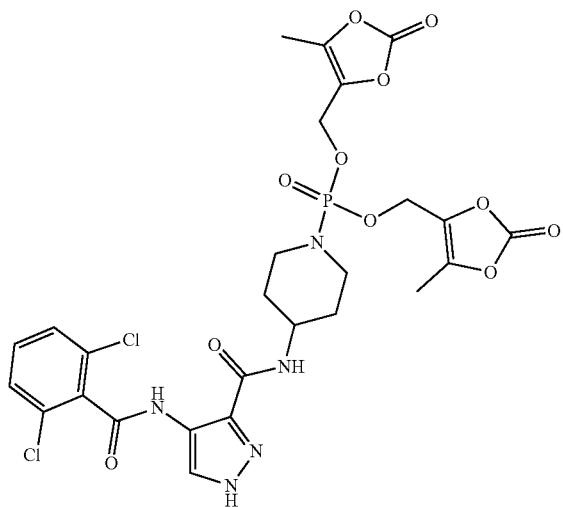 [SMILES: Cc1oc(=O)oc1COP(=O)(OCc1oc(=O)oc1C)N1CCC(NC(=O)c2n[nH]cc2NC(=O)c2c(Cl)cccc2Cl)CC1] |
| 54 | 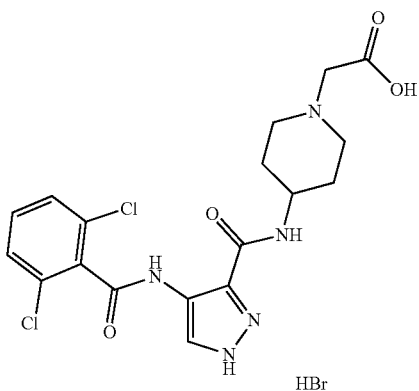 [SMILES: O=C(O)CN1CCC(NC(=O)c2n[nH]cc2NC(=O)c2c(Cl)cccc2Cl)CC1 ; Br] |
| 55 | 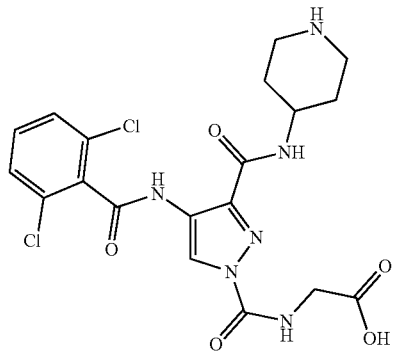 [SMILES: O=C(O)CNC(=O)n1cc(NC(=O)c2c(Cl)cccc2Cl)c(C(=O)NC2CCNCC2)n1] |

TABLE 1-continued

Examples of compounds of Formula I.

| No. | Structure |
|---|---|
| 56 | 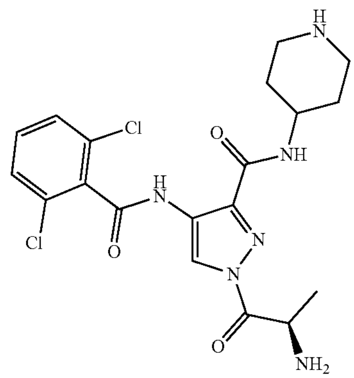 [SMILES: C[C@@H](N)C(=O)n1cc(NC(=O)c2c(Cl)cccc2Cl)c(C(=O)NC2CCNCC2)n1] |
| 57 | 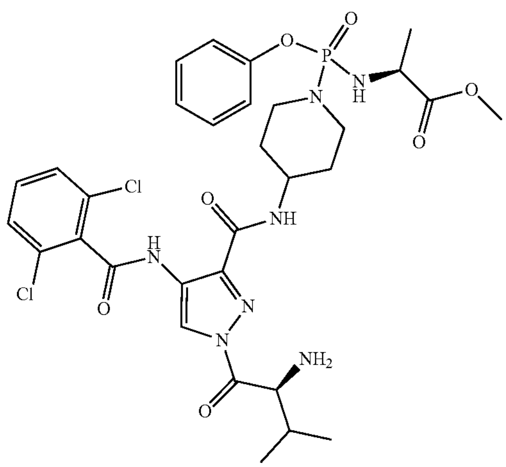 [SMILES: COC(=O)[C@H](C)NP(=O)(Oc1ccccc1)N1CCC(NC(=O)c2nn(C(=O)[C@@H](N)C(C)C)cc2NC(=O)c2c(Cl)cccc2Cl)CC1] |
| 58 | 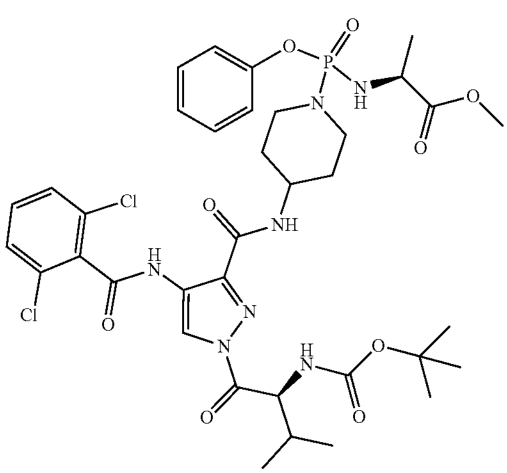 [SMILES: COC(=O)[C@H](C)NP(=O)(Oc1ccccc1)N1CCC(NC(=O)c2nn(C(=O)[C@@H](NC(=O)OC(C)(C)C)C(C)C)cc2NC(=O)c2c(Cl)cccc2Cl)CC1] |

TABLE 1-continued
Examples of compounds of Formula I.
| No. | Structure |
|---|---|
| 59 | 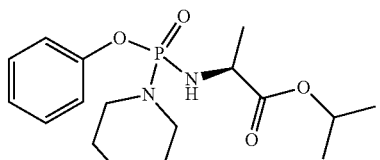 |
| 60 | 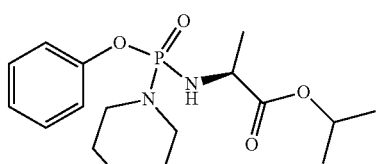 |
| 61 | 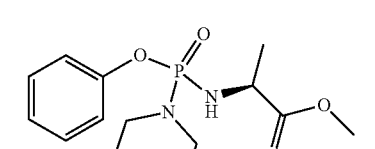 |

TABLE 1-continued
Examples of compounds of Formula I.
| No. | Structure |
|---|---|
| 62 | 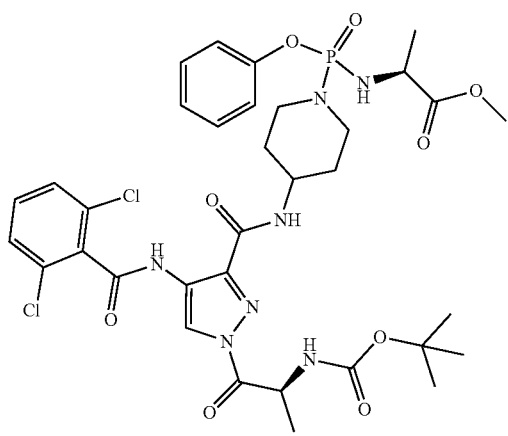 [SMILES: COC(=O)[C@H](C)NP(=O)(Oc1ccccc1)N1CCC(NC(=O)c2nn(C(=O)[C@H](C)NC(=O)OC(C)(C)C)cc2NC(=O)c2c(Cl)cccc2Cl)CC1] |
| 63 | 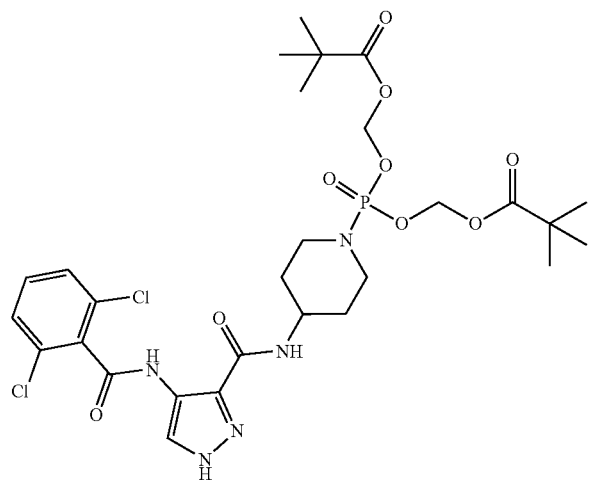 [SMILES: CC(C)(C)C(=O)OCOP(=O)(OCOC(=O)C(C)(C)C)N1CCC(NC(=O)c2n[nH]cc2NC(=O)c2c(Cl)cccc2Cl)CC1] |
| 64 | 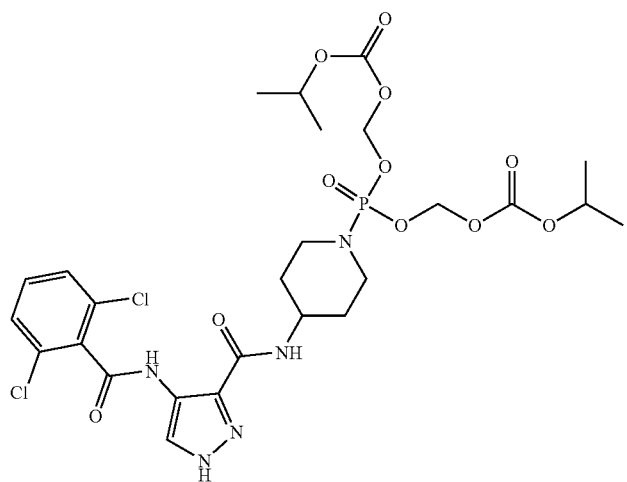 [SMILES: CC(C)OC(=O)OCOP(=O)(OCOC(=O)OC(C)C)N1CCC(NC(=O)c2n[nH]cc2NC(=O)c2c(Cl)cccc2Cl)CC1] |

TABLE 1-continued
Examples of compounds of Formula I.
| No. | Structure |
|---|---|
| 65 | 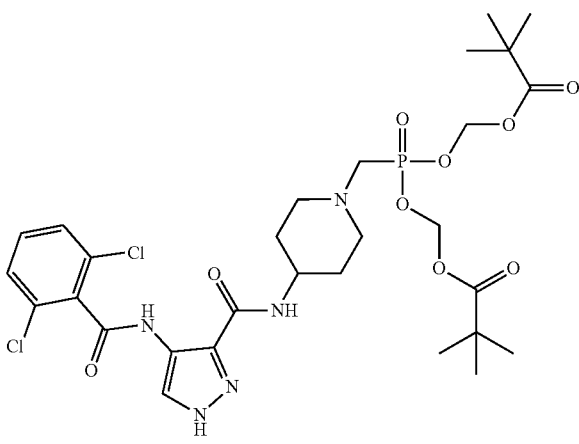 [SMILES: CC(C)(C)C(=O)OCOP(=O)(CN1CCC(NC(=O)c2n[nH]cc2NC(=O)c2c(Cl)cccc2Cl)CC1)OCOC(=O)C(C)(C)C] |
| 66 | 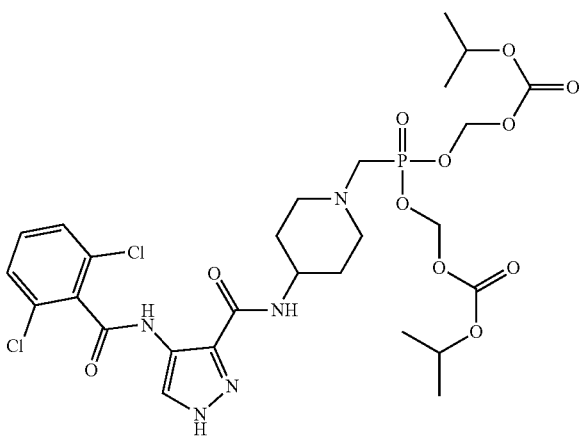 [SMILES: CC(C)OC(=O)OCOP(=O)(CN1CCC(NC(=O)c2n[nH]cc2NC(=O)c2c(Cl)cccc2Cl)CC1)OCOC(=O)OC(C)C] |
| 67 | 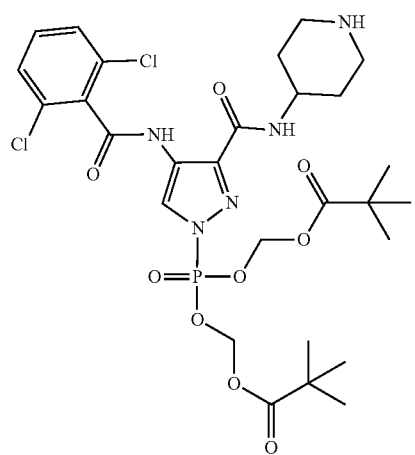 [SMILES: CC(C)(C)C(=O)OCOP(=O)(OCOC(=O)C(C)(C)C)n1cc(NC(=O)c2c(Cl)cccc2Cl)c(C(=O)NC2CCNCC2)n1] |

TABLE 1-continued

Examples of compounds of Formula I.

| No. | Structure |
|---|---|
| 68 | 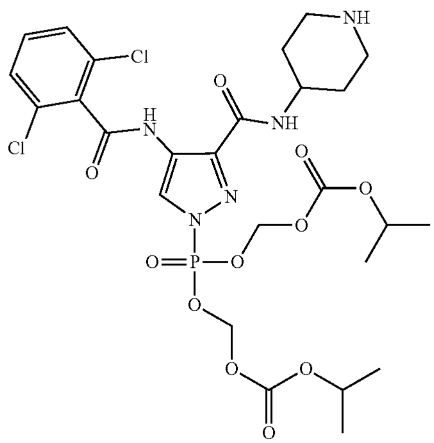 [SMILES: CC(C)OC(=O)OCOP(=O)(OCOC(=O)OC(C)C)n1cc(NC(=O)c2c(Cl)cccc2Cl)c(C(=O)NC2CCNCC2)n1] |
| 69 | 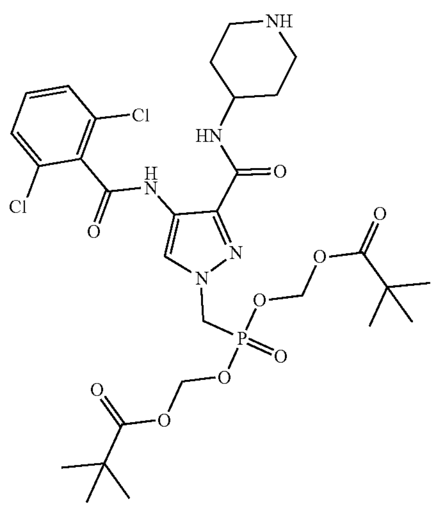 [SMILES: CC(C)(C)C(=O)OCOP(=O)(Cn1cc(NC(=O)c2c(Cl)cccc2Cl)c(C(=O)NC2CCNCC2)n1)OCOC(=O)C(C)(C)C] |
| 70 | 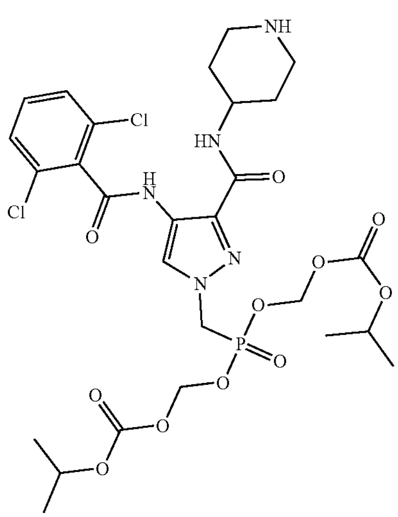 [SMILES: CC(C)OC(=O)OCOP(=O)(Cn1cc(NC(=O)c2c(Cl)cccc2Cl)c(C(=O)NC2CCNCC2)n1)OCOC(=O)OC(C)C] |

TABLE 1-continued

Examples of compounds of Formula I.

| No. | Structure |
|---|---|
| 71 | 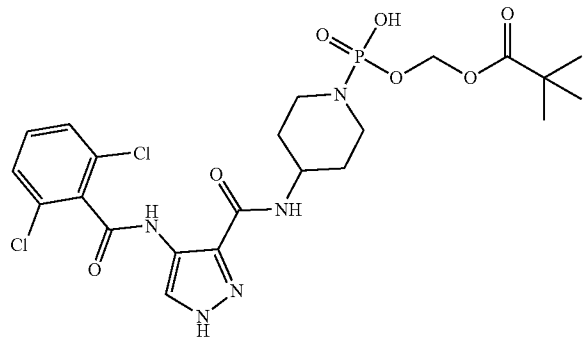 [SMILES: CC(C)(C)C(=O)OCOP(=O)(O)N1CCC(NC(=O)c2n[nH]cc2NC(=O)c2c(Cl)cccc2Cl)CC1] |
| 72 | 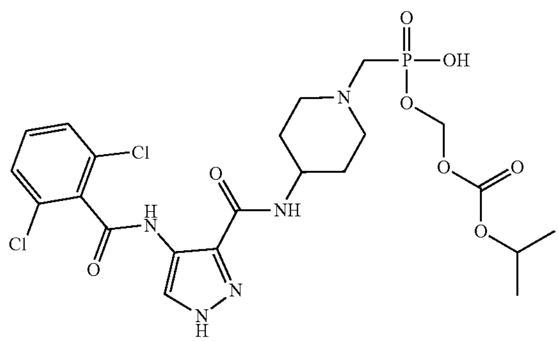 [SMILES: CC(C)OC(=O)OCOP(=O)(O)CN1CCC(NC(=O)c2n[nH]cc2NC(=O)c2c(Cl)cccc2Cl)CC1] |
| 73 | 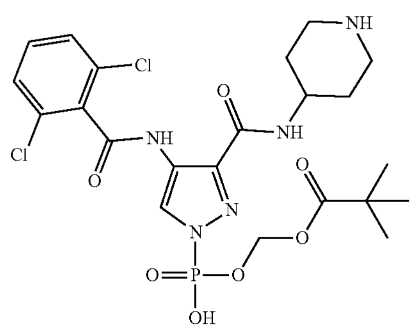 [SMILES: CC(C)(C)C(=O)OCOP(=O)(O)n1cc(NC(=O)c2c(Cl)cccc2Cl)c(C(=O)NC2CCNCC2)n1] |
| 74 | 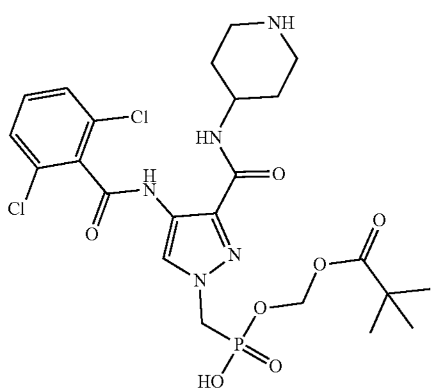 [SMILES: CC(C)(C)C(=O)OCOP(=O)(O)Cn1cc(NC(=O)c2c(Cl)cccc2Cl)c(C(=O)NC2CCNCC2)n1] |

In some embodiments, compounds provided herein are inhibitors of cyclin dependent kinases, and in particular cyclin dependent kinases selected from CDK1, CDK2, CDK3, CDK4, CDK5, CDK6, CDK7 and CDK9. In some embodiments, compounds can inhibit one or more CDK kinase selected from CDK1, CDK2, CDK4, CDK5, CDK6, and CDK9. In an embodiment, the compound inhibits CDK1, CDK2, or both CDK1 and CDK2. In an embodiment, the compound inhibits CDK4, CDK6, or both CDK4 and CDK6. In embodiments, compounds provided herein are, additionally or alternatively, inhibitors of glycogen synthase kinase-3 (GSK3).

In some embodiments, compounds provided herein are prodrugs of AT7519.

In a second broad aspect, there are provided pharmaceutical compositions comprising a compound described herein, or a pharmaceutically acceptable salt or ester thereof, and a pharmaceutically acceptable carrier. In some embodiments, there are provided pharmaceutical compositions comprising a compound of Formula I, or a pharmaceutically acceptable salt or ester thereof, and a pharmaceutically acceptable carrier.

In a third broad aspect, there are provided methods of inhibiting or modulating the activity of a cyclin dependent kinase (CDK) and/or glycogen synthase kinase-3 (GSK-3). In some embodiments, there are provided methods of treating disease states or conditions mediated by cyclin dependent kinases and/or glycogen synthase kinase-3 in a subject in need thereof comprising administering to the subject an effective amount of a compound and/or a pharmaceutical composition described herein. Non-limiting examples of disease states or conditions mediated by cyclin dependent kinases and/or glycogen synthase kinase-3 that may be treated according to methods provided herein include viral infections, type II or non-insulin dependent diabetes mellitus, autoimmune diseases, head trauma, stroke, epilepsy, neurodegenerative diseases such as Alzheimer's, motor neuron disease, progressive supranuclear palsy, corticobasal degeneration and Pick's disease, and disorders of proliferation, apoptosis or differentiation, such as various tumors and cancers. In particular embodiments, compounds are useful for treatment of viral infections, autoimmune diseases and/or neurodegenerative diseases.

In other embodiments, compounds are useful for treatment of tumors and cancers. Examples of tumors and cancers that may be treated according to methods provided herein include, without limitation: multiple myeloma (MM), chronic lymphocytic leukemia (CLL), acute myeloid leukemia (AML), mantle cell lymphoma (MCL), solid tumors, refractory solid tumors, non-Hodgkin lymphoma, carcinoma of the colon, hematological neoplasm, and myelodysplastic syndromes (MDS). Other tumors and cancers include, without limitation: neuroblastoma, colorectal cancer, cervical cancer, lung cancer, leukemia, breast cancer, pancreatic cancer, B-cell malignancies, neoplasms, and metastatic tumors.

In some embodiments, compounds provided herein and/or pharmaceutical compositions thereof are administered to reduce the therapeutic toxicity and/or adverse effects, and/or increase tolerability of AT7519, and/or improve therapeutic effect in a subject, as compared to administration of AT7519.

In other embodiments, compounds provided herein and/or pharmaceutical compositions thereof are administered to improve biodistribution of AT7519, to reduce the side effects of AT7519, and/or to broaden the therapeutic application (such as dose regimen, including the routes of administration, dose frequency, and maximum tolerated dose, etc.) in a subject, as compared to administration of AT7519 itself.

In another broad aspect, there are provided kits comprising one or more compound or pharmaceutical composition described herein. A kit may further comprise one or more additional therapeutic agents and/or instructions, for example, instructions for using the kit to treat a subject having disease states or conditions mediated by cyclin dependent kinases and/or glycogen synthase kinase-3.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Definitions

Figure 1:
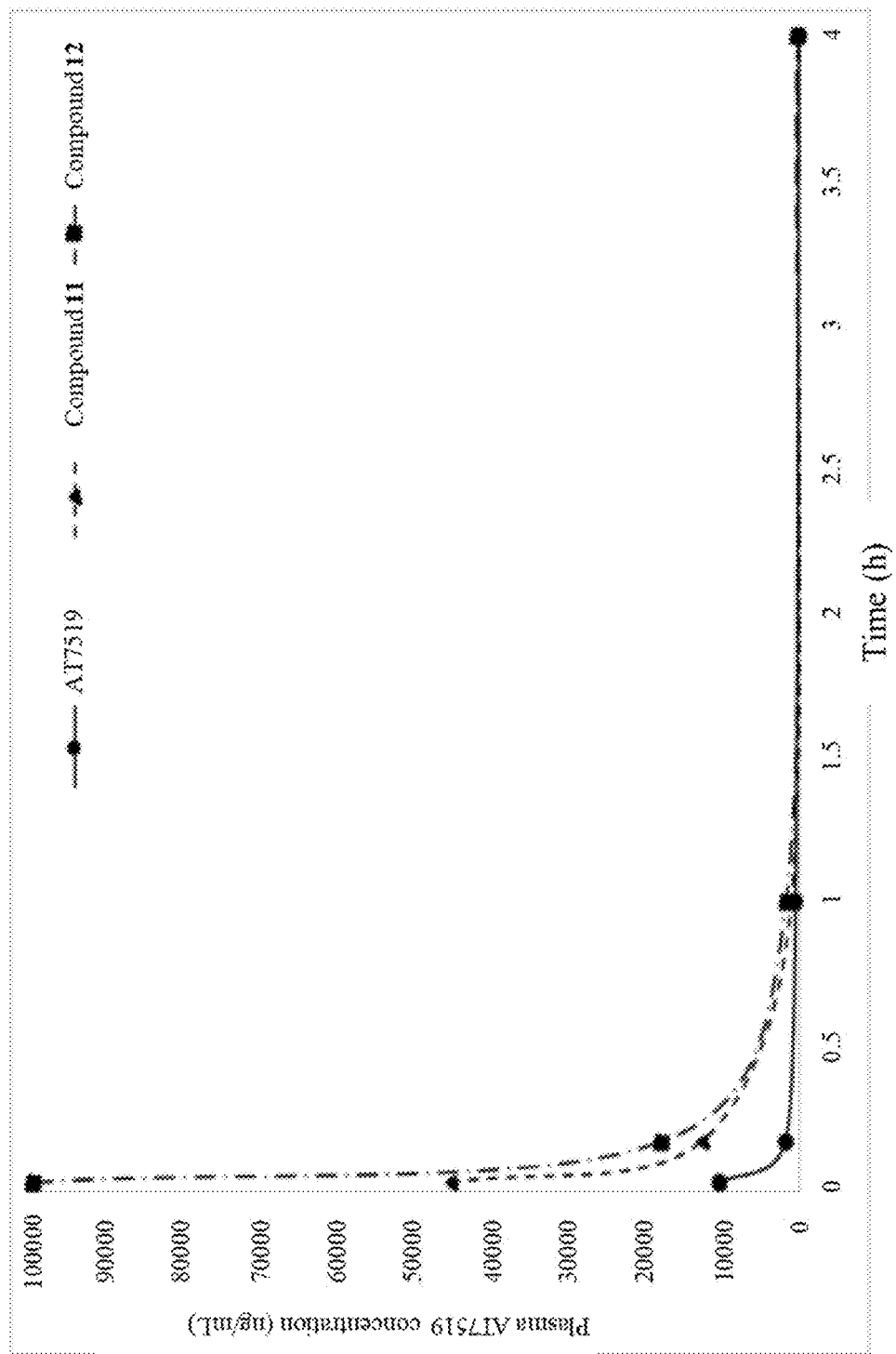
FIG. 1 shows plasma AT7519 concentration-time curves after intravenous administration of AT7519, compound 11, and compound 12 to mice.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "derivative" as used herein, is understood as being a substance similar in structure to another compound but differing in some slight structural detail.

The present description refers to a number of chemical terms and abbreviations used by those skilled in the art. Nevertheless, definitions of selected terms are provided for clarity and consistency.

As used herein, the term "substituted" or "with substitution" refers to a parent compound or a moiety has at least one (1) substituent group. The term "unsubstituted" or "without substitution" refers to a parent compound or a moiety has no other substituent group except that the unidentified valence is chemically saturated with hydrogen atoms.

As used herein, a "substituent" or a "substituent group" refers to a group selected from halogen (F, Cl, Br, or I), hydroxy, sulfhydryl, amino, nitro, carbonyl, carboxyl, alkyl, alkoxyl, alkylamino, aryl, aryloxyl, acylamino, acyl, thionyl, sulfonyl, phosphonyl, or other organic moiety as used and accepted in general organic chemistry.

As used herein, the term "alkyl" refers to saturated hydrocarbons having from one to twelve carbon atoms, including linear, branched, and cyclic alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, cyclopropyl, cyclopentyl, cyclohexyl, cycloheptyl, cyclooctyl, and the like. The term alkyl includes both unsubstituted alkyl groups and substituted alkyl groups. The term "$C_1$-$C_n$alkyl", wherein n is an integer from 2 to 12, refers to an alkyl group having from 1 to the indicated "n" number of carbon atoms. Alkyl residues may be substituted or unsubstituted. In some embodiments, for example, alkyl may be substituted by hydroxyl, amino, carboxyl, carboxylic ester, amide, carbamate, or aminoalkyl.

Unless the number of carbons is otherwise specified, "lower" as in "lower aliphatic," "lower alkyl," "lower alkenyl," and "lower alkylnyl", as used herein means that the moiety has at least one (two for alkenyl and alkynyl) and equal to or less than 6 carbon atoms.

The terms "cycloalkyl", "alicyclic", "carbocyclic" and equivalent expressions refer to a group comprising a saturated or partially unsaturated carbocyclic ring in a single, spiro (sharing one atom), or fused (sharing at least one bond) carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl", wherein n is an integer from 4 to 15, refers to a cycloalkyl group having from 3 to the indicated "n" number of carbon atoms in the ring structure. Unless the number of carbons is otherwise specified, "lower cycloalkyl" groups as herein used, have at least 3 and equal to or less than 8 carbon atoms in their ring structure.

Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_{1-4}$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

The term "heterocycloalkyl" and equivalent expressions refer to a group comprising a saturated or partially unsaturated carbocyclic ring in a single, spiro (sharing one atom), or fused (sharing at least one bond) carbocyclic ring system having from three to fifteen ring members, including one to six heteroatoms (e.g., N, O, S, P) or groups containing such heteroatoms (e.g., NH, $NR_x$ ($R_x$ is alkyl, acyl, aryl, heteroaryl or cycloalkyl), $PO_2$, SO, $SO_2$, and the like). Heterocycloalkyl groups may be C-attached or heteroatom-attached (e.g., via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and sugars, and the like. The term heterocycloalkyl includes both unsubstituted heterocycloalkyl groups and substituted heterocycloalkyl groups. The term "$C_3$-$C_n$heterocycloalkyl", wherein n is an integer from 4 to 15, refers to a heterocycloalkyl group having from 3 to the indicated "n" number of atoms in the ring structure, including at least one hetero group or atom as defined above. Unless the number of carbons is otherwise specified, "lower heterocycloalkyl" groups as herein used, have at least 3 and equal to or less than 8 carbon atoms in their ring structure.

The terms "aryl" and "aryl ring" refer to aromatic groups having "4n+2".pi.(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-$C_n$aryl", wherein n is an integer from 6 to 15, refers to an aryl group having from 6 to the indicated "n" number of atoms in the ring structure, including at least one hetero group or atom as defined above.

The terms "heteroaryl" and "heteroaryl ring" refer to an aromatic groups having "4n+2".pi.(pi) electrons, wherein n is an integer from 1 to 3, in a conjugated monocyclic or polycyclic system (fused or not) and having five to fourteen ring members, including one to six heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g., via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrollyl, quinolinyl, isoquinolinyl, indolyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_5$-$C_n$heteroaryl", wherein n is an integer from 6 to 15, refers to a heteroaryl group having from 5 to the indicated "n" number of atoms in the ring structure, including at least one hetero group or atom as defined above.

The terms "heterocycle" or "heterocyclic" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula —NR$^a$R$^b$, in which R$^a$ and R$^b$ are each independently hydrogen, alkyl, aryl, or heterocyclyl, or R$^a$ and R$^b$, taken together with the nitrogen atom to which they are attached, form a heterocyclic ring. The term amino includes compounds or moieties in which a nitrogen atom is covalently bonded to at least one carbon or heteroatom. Thus, the terms "alkylamino" and "dialkylamino" as used herein mean an amine group having respectively one and at least two $C_1$-$C_6$alkyl groups attached thereto. The terms "arylamino" and "diarylamino" include groups wherein the nitrogen is bound to at least one or two aryl groups, respectively. The terms "amide" or "aminocarbonyl" include compounds or moieties which contain a nitrogen atom which is bound to the carbon of a carbonyl or a thiocarbonyl group. The term "acylamino" refers to an amino group directly attached to an acyl group as defined herein.

The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The terms "alkoxy" or "lower alkoxy" as used herein mean an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups, and the like. The term "alkoxy" includes both unsubstituted or substituted alkoxy groups, etc., as well as perhalogenated alkyloxy groups.

The terms "carbonyl" or "carboxy" include compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group (C1-C6alkyl, C1-C6alkenyl, C1-C6alkynyl, e.g., acetyl), a cycloalkyl group (C3-C8cycloalkyl), a heterocyclic group (C3-C8 heterocycloalkyl and C5-C6 heteroaryl), an aromatic group (C6 aryl, e.g., benzoyl), and the like. Acyl groups may be unsubstituted or substituted acyl groups (e.g., salicyloyl).

The term "solvate" refers to a physical association of a compound with one or more solvent molecules, whether organic or inorganic. This physical association includes hydrogen bonding. In certain instances, a solvate will be capable of isolation, for example when one or more solvent molecules are incorporated in the crystal lattice of a crystalline solid. "Solvate" encompasses both solution-phase and isolable solvates. Exemplary solvates include, without limitation, hydrates, ethanolates, methanolates, hemiethanolates, and the like. The term "hydrate" refers to a physical association of a compound with water molecules.

The term "chelate" refers to a physical association of a compound with a central metal atom, typically bonded at two or more points, often in a cyclic or ring structure.

It should be understood that compounds described herein may contain one or more chiral centers and/or double bonds and therefore, may exist as stereoisomers, such as double-bond isomers (i.e., geometric isomers), enantiomers, or diastereomers. Chemical structures disclosed herein are intended to encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan, e.g., chiral chromatography (such as chiral HPLC), immunoassay techniques, or the use of covalently (such as Mosher's esters) and non-covalently (such as chiral salts) bound chiral reagents to respectively form a diastereomeric mixture which can be separated by conventional methods, such as chromatography, distillation, crystallization or sublimation, the chiral salt or ester is then exchanged or cleaved by conventional means, to recover the desired isomers. The compounds may also exist in several tautomeric forms including the enol form, the keto form, and mixtures thereof. The chemical structures depicted herein are also intended to encompass all possible tautomeric forms of the illustrated compounds.

Certain compounds may exist in multiple crystalline or amorphous forms. In general, all physical forms are intended to be encompassed herein. The term "polymorphic form" refers to the various physical forms that a compound may display.

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that take advantage of an intrinsically basic, acidic or charged functionality on the molecule and that are not biologically or otherwise undesirable. Examples of pharmaceutically acceptable salts are also described, for example, in Berge et al., "Pharmaceutical Salts", J. Pharm. Sci. 66, 1-19 (1977). Non-limiting examples of such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the parent compound either is replaced by a metal ion, including, an alkali metal ion (e.g., lithium, sodium, potassium), an alkaline earth ion (e.g., magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from a parent compound that contains a basic or acidic moiety, by conventional chemical methods. Generally, such salts are prepared by reacting the free acid or base forms of compounds with a stoichiometric amount of the appropriate base or acid in water or in an organic solvent, or in a mixture of the two. Salts may be prepared in situ, during the final isolation or purification of a compound or by separately reacting a compound in its free acid or base form with the desired corresponding base or acid, and isolating the salt thus formed. The term "pharmaceutically acceptable salts" also include zwitterionic compounds containing a cationic group covalently bonded to an anionic group, as they are "internal salts". It should be understood that all acid, salt, base, and other ionic and non-ionic forms of compounds described herein are intended to be encompassed. For example, if a compound is shown as an acid herein, the salt forms of the compound are also encompassed. Likewise, if a compound is shown as a salt, the acid and/or basic forms are also encompassed.

As used herein the term "effective amount" refers to the amount or dose of a therapeutic agent, such as a compound, upon single or multiple dose administration to a subject, which provides the desired therapeutic, diagnostic, or prognostic effect in the subject. An effective amount can be readily determined by an attending physician or diagnostician using known techniques and by observing results obtained under analogous circumstances. In determining the effective amount or dose of compound administered, a number of factors are considered including, but not limited to: the size, age, and general health of the subject; the specific disease involved; the degree of or involvement or the severity of the disease or condition to be treated; the response of the individual subject; the particular compound administered; the mode of administration; the bioavailability characteristics of the preparation administered; the dose regimen selected; the use of concomitant medication(s); and other relevant considerations.

"Pharmaceutically acceptable" refers to drugs, medicaments, inert ingredients etc., which the term describes, suitable for use in contact with the cells or tissues of humans and animals without undue toxicity, incompatibility, instability, irritation, allergic response, and the like, commensurate with a reasonable benefit/risk ratio. It generally refers to a compound or composition that is approved or approvable by a regulatory agency of the Federal or state government or listed in the U.S. Pharmacopoeia or other generally recognized pharmacopoeia for use in animals and more particularly in humans.

"Pharmaceutically acceptable vehicle" refers to a diluent, adjuvant, excipient, vehicle or carrier with which a compound is administered. The terms "Pharmaceutically acceptable vehicle" and "Pharmaceutically acceptable carrier" are used interchangeably herein.

"Pharmaceutical composition" refers to a composition comprising a compound as described herein and at least one component comprising a pharmaceutically acceptable carrier, diluent, adjuvant, excipient, or vehicle, such as a preserving agent, a filler, a disintegrating agent, a wetting agent, an emulsifying agent, a suspending agent, a sweetening agent, a flavoring agent, a perfuming agent, an antibacterial agent, an antifungal agent, a lubricating agent, a dispensing agent, and the like, depending on the nature of the mode of administration and dosage forms.

"Preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease).

"Treating" or "treatment" of any disease or disorder refers, in some embodiments, to ameliorating at least one disease or disorder. In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In some embodiments, "treating" or "treatment" refers to improving the quality of life or reducing the symptoms or side effects of a disease in a subject in need thereof "Therapeutically effective amount" means the amount of a compound that, when administered to a subject for treating or preventing a disease, is sufficient to effect such treatment or prevention of the disease. The "therapeutically effective amount" will vary depending on the compound, the disease and its severity, and the age, weight, etc., of the subject having the disease to be treated or prevented. As used herein, the term "therapeutically effective amount" refers to an amount of a compound or composition sufficient to prevent, treat, inhibit, reduce, ameliorate or eliminate one or more causes, symptoms, or complications of a disease such as a cancer.

The term "subject" includes animals, including mammals and humans, particularly humans.

The term "prodrug" and equivalent expressions refer to agents which can be converted in vitro or in vivo directly or indirectly to an active form (see, e.g., R. B. Silverman, 1992, "The Organic Chemistry of Drug Design and Drug Action," Academic Press, Chap. 8; Bundgaard, Hans; Editor. Neth. (1985), "Design of Prodrugs". 360 pp. Elsevier, Amsterdam; Stella, V.; Borchardt, R.; Hageman, M.; Oliyai, R.; Maag, H.; Tilley, J. (Eds.) (2007), "Prodrugs: Challenges and Rewards, XVIII, 1470 p. Springer). Prodrugs can be used to alter the bio-distribution (e.g., to allow agents which would not typically enter the reactive site of a protease) or the pharmacokinetics for a particular agent. A wide variety of groups have been used to modify compounds to form prodrugs, for example, esters, ethers, phosphates, etc. When a prodrug is administered to a subject, the group is cleaved, enzymatically or non-enzymatically, reductively, oxidatively, or hydrolytically, or otherwise to reveal the active form. As used herein, "prodrug" includes pharmaceutically acceptable salts or esters thereof, or pharmaceutically acceptable solvates or chelates as well as crystalline forms of any of the foregoing.

Prodrugs are frequently, although not necessarily, pharmacologically inactive until converted to the active form. "Inactive" prodrugs are pharmacologically inactive medications that are metabolized into an active form within the body. For example, instead of administering a drug directly, a corresponding prodrug might be used instead to improve how a medicine is absorbed, distributed, metabolized, and excreted (ADME) (for examples, see Malhotra, B., et al., "The design and development of fesoterodine as a prodrug of 5-hydroxymethyl tolterodine (5-HMT), the active metabolite of tolterodine", *Curr. Med. Chem.,* 2009, 16 (33): 4481-9; and Stella, V. J., et al, "Prodrugs. Do they have advantages in clinical practice?". *Drugs,* 1985. 29 (5): 455-73). A prodrug may be used to improve how selectively a drug interacts with cells or processes that are not its intended target. This can reduce adverse or unintended effects of a drug, especially important in treatments like chemotherapy, which can have severe unintended and undesirable side effects. For example, Tenofovir alafenamide (TAF), a novel prodrug of tenofovir, was developed to deliver enhanced antiviral potency and reduced systemic toxicities (Byrne, R., et al, *Therap. Adv. Gastroenterol.,* 2018, 11:1-12).

The term "ester" refers to compounds that can be represented by the formula RCOOR (carboxylic ester) or the formula RSO3R' (sulfonate ester), usually respectively formed by the reaction between a carboxylic or a sulfonic acid and an alcohol usually with the elimination of water.

The term "amino acid" generally refers to an organic compound comprising both a carboxylic acid group and an amine group. The term "amino acid" includes both "natural" and "unnatural" or "non-natural" amino acids. Additionally, the term amino acid includes O-alkylated and N-alkylated amino acids, as well as amino acids having nitrogen or oxygen-containing side chains (such as Lys, Cys, or Ser) in which the nitrogen or oxygen atom has been acylated or alkylated. Amino acids may be pure L or D isomers or mixtures of L and D isomers, including (but not limited to) racemic mixtures.

The term "natural amino acid" and equivalent expressions refer to L-amino acids commonly found in naturally-occurring proteins. Examples of natural amino acids include, without limitation, alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), tyrosine (Tyr), β-alanine (β-Ala), and γ-aminobutyric acid (GABA).

The term "unnatural amino acid" refers to any derivative of a natural amino acid including D forms, and α- and β-amino acid derivatives. The terms "unnatural amino acid" and "non-natural amino acid" are used interchangeably herein. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): 2-aminoadipic acid (Aad), 3-aminoadipic acid (β-Aad), 2-aminobutyric acid (2-Abu), α,β-dehydro-2-aminobutyric acid (8-AU), 1-aminocyclopropane-1-carboxylic acid (ACPC), aminoisobutyric acid (Aib), 3-aminoisobutyric acid (β-Aib), 2-amino-thiazoline-4-carboxylic acid, 5-aminovaleric acid (5-Ava), 6-aminohexanoic acid (6-Ahx), 2-aminoheptanoic acid (Ahe), 8-aminooctanoic acid (8-Aoc), 11-aminoundecanoic acid (11-Aun), 12-aminodo-decanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxy-pentanoic acid (ACHPA), para-aminophenylalanine (4-NH2-Phe), 2-aminopimelic acid (Apm), biphenylalanine (Bip), para-bromophenylalanine (4-Br-Phe), ortho-chlorophenylalanine (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), desmosine (Des), 2,2-di-aminopimelic acid (Dpm), 2,3-diaminopropionic acid (Dpr), 2,4-diaminobutyric acid (Dbu), 3,4-dichlorophenylalanine (3,4-Cl-2-Phe), 3,4-difluororphenylalanine (3,4-F2-Phe), 3,5-diiodotyrosine (3,5-I2-Tyr), N-ethylglycine (EtGly), N-ethylasparagine (EtAsn), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), hydroxylysine (Hyl), allo-hydroxylysine (aHyl), 5-hydroxytryptophan (5-OH-Trp), 3- or 4-hydroxyproline (3- or 4-Hyp), para-iodophenylalanine (4-I-Phe), 3-iodotyrosine (3-I-Tyr), indoline-2-carboxylic acid (Idc), isodesmosine (Ide), allo-isoleucine (a-Ile), isonipecotic acid (Inp), N-methylisoleucine (MeIle), N-methyllysine (MeLys), meta-methyltyrosine (3-Me-Tyr), N-methylvaline (MeVal), 1-naphthylalanine (1-Nal), 2-naphthylalanine (2-Nal), para-nitrophenylalanine (4-NO2-Phe), 3-nitrotyrosine (3-NO2-Tyr), norleucine (Nle), norvaline (Nva), ornithine (Orn), ortho-phosphotyrosine (H2PO3-Tyr), octahydroindole-2-carboxylic acid (Oic), penicillamine (Pen), pentafluorophenylalanine (F5-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th).

For compounds provided herein, it is intended that, in some embodiments, salts thereof are also encompassed, including pharmaceutically acceptable salts. Those skilled in the art will appreciate that many salt forms (e.g., TFA salt, tetrazolium salt, sodium salt, potassium salt, etc,) are possible; appropriate salts are selected based on considerations known in the art. The term "pharmaceutically acceptable salt" refers to salts prepared from pharmaceutically acceptable non-toxic acids or bases including inorganic acids and bases and organic acids and bases. For example, for compounds that contain a basic nitrogen, salts may be prepared from pharmaceutically acceptable non-toxic acids including inorganic and organic acids. Suitable pharmaceutically acceptable acid addition salts for the compounds of the present invention include without limitation acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include without limitation metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

Compositions

Compounds are generally administered in the form of a pharmaceutical composition (e.g., formulation) comprising at least one active compound of the present technology together with one or more pharmaceutically acceptable carriers, adjuvants, excipients, diluents, fillers, buffers, stabilisers, preservatives, lubricants, or other materials well known to those skilled in the art, and optionally other therapeutic or prophylactic agents. Thus, there are further provided pharmaceutical compositions, and methods of making a pharmaceutical composition comprising admixing at least one active compound, as defined above, together with one or more pharmaceutically acceptable carriers, excipients, buffers, adjuvants, stabilizers, or other materials, as described herein.

Pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. In one particular embodiment, the pharmaceutical composition is in a form suitable for intravenous (i.v.) administration, for example by injection or infusion. In another particular embodiment, the pharmaceutical composition is in a form suitable for subcutaneous (s.c.) administration.

Pharmaceutical dosage forms suitable for oral administration include, for example and without limitation, tablets, capsules, caplets, pills, lozenges, syrups, solutions, powders, granules, elixirs and suspensions, sublingual tablets, wafers or patches and buccal patches.

Pharmaceutical compositions containing compounds provided herein can be formulated in accordance with known techniques, see for example, Remington's Pharmaceutical Sciences, Mack Publishing Company, Easton, Pa., USA.

In some embodiments, compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable cross-linked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well-known.

Capsule formulations may be of the hard gelatin or soft gelatin variety and can contain the active component in solid, semi-solid, or liquid form. Gelatin capsules can be formed from animal gelatin or synthetic or plant derived equivalents thereof.

Solid dosage forms (tablets, capsules, etc.) can be coated or un-coated, but typically have a coating, for example a protective film coating (e.g., a wax or varnish) or a release controlling coating. The coating (e.g. a Eudragit™ type polymer) can be designed to release the active component at a desired location within the gastrointestinal tract. Thus, the coating can be selected so as to degrade under certain pH conditions within the gastrointestinal tract, thereby selectively release the compound in the stomach or in the ileum or duodenum.

Instead of, or in addition to, a coating, the compound can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g., a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example, intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

Compounds may also be presented in unit dosage form and, as such, will typically contain sufficient compound to provide a desired level of biological activity. The phrase "unit dosage form" refers to physically discrete units, each unit containing a predetemlined amount of the active compound, either alone or in combination with one or more additional agents, sufficient to produce the desired effect. It will be appreciated that the parameters of a unit dosage form will depend on the particular agent(s) and the effect to be achieved.

In some embodiments, the pharmaceutical composition is provided in a single-use container (e.g., a single-use vial, ampoule, syringe, or autoinjector, whereas a multi-use container (e.g., a multi-use vial) is provided in other embodiments.

In some embodiments, a compound may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect. For administration of an oral agent, the compositions can be provided in the form of tablets, capsules and the like containing from 1.0 to 1000 milligrams of the active ingredient, particularly 1, 3, 5, 10, 15, 20, 25, 50, 75, 100, 150, 200, 250, 300, 400, 500, 600, 750, 800, 900, or 1000 milligrams of the active ingredient. For example, a formulation intended for oral administration may contain from 0.1 milligrams to 2 grams of active ingredient, more usually from 10 milligrams to 1 gram, for example, from 50 milligrams to 500 milligrams.

In some embodiments, there is provided a composition comprising a compound as described herein and at least one component comprising a pharmaceutically acceptable carrier, diluent, adjuvant, excipient, or vehicle, such as a preserving agent, a filler, a disintegrating agent, a wetting agent, an emulsifying agent, a suspending agent, a sweetening agent, a flavoring agent, a perfuming agent, an antibacterial agent, an antifungal agent, a lubricating agent, or a dispensing agent.

In an embodiment, there is provided a pharmaceutical composition comprising a compound of the invention, e.g., a compound of Formula I, or a pharmaceutically acceptable salt, ester, or solvate thereof, and a pharmaceutically acceptable carrier. In an embodiment, there is provided a pharmaceutical composition comprising a compound in Table 1, or a pharmaceutically acceptable salt or ester thereof, and a pharmaceutically acceptable carrier. In another embodiment, there is provided a pharmaceutical composition comprising a compound of Formula I or a compound in Table 1, or a pharmaceutically acceptable salt or ester thereof, and a pharmaceutically acceptable carrier.

In another embodiment, compounds and/or compositions of the invention are administered to a subject via various routes, including for example and without limitation, intravenous (i.v.) administration, oral (p.o.) administration, intragastric (i.g.) administration, intraperitoneal (i.p.) administration, intramuscular (i.m.) administration, subcutaneous (s.c.) administration, parenteral administration, etc., for delivering the compound effectively.

Methods of Use

Compounds provided herein inhibit cyclin dependent kinases, e.g., one or more cyclin dependent kinase selected from CDK1, CDK2, CDK3, CDK4, CDK5, CDK6, CDK7 and CDK9, and/or glycogen synthase kinase-3 (GSK3). By means of their activity in modulating or inhibiting CDK kinases and glycogen synthase kinase, compounds are expected to be useful in providing a means of arresting, or recovering control of, the cell cycle in abnormally dividing cells. It is therefore anticipated that the compounds will prove useful in treating or preventing proliferative disorders such as cancers. It is also envisaged that the compounds of the invention may be useful in treating conditions such as, for example and without limitation, viral infections, type II or non-insulin dependent diabetes mellitus, autoimmune diseases, head trauma, stroke, epilepsy, neurodegenerative diseases such as Alzheimer's, motor neuron disease, progressive supranuclear palsy, corticobasal degeneration and Pick's disease. In particular embodiments, compounds are useful for treatment of viral infections, autoimmune diseases and/or neurodegenerative diseases.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation, such as cancer and tumors. Examples of cancers which may be inhibited or treated in accordance with the present technology include, but are not limited to, a carcinoma, for example a carcinoma of the bladder, breast, colon (e.g., colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g., exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma, a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

The cancers to be treated or inhibited may be cancers which are sensitive to inhibition of any one or more cyclin dependent kinase selected from CDK1, CDK2, CDK3, CDK4, CDK5, CDK6, CDK7, and CDK9, for example, one or more CDK kinases selected from CDK1, CDK2, CDK4, CDK5, CDK6, and CDK9, e.g., CDK1 and/or CDK2, CDK4 and/or CDK6, etc.

CDKs are also known to play a role in apoptosis, proliferation, differentiation and transcription and therefore CDK inhibitors could also be useful in the treatment of the following diseases other than cancer: viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

Thus, in the pharmaceutical compositions, uses or methods of this invention for treating a disease or condition comprising abnormal cell growth, the disease or condition comprising abnormal cell growth in one embodiment is a cancer. One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers. Another sub-set of cancers includes breast cancer, ovarian cancer, colon cancer, prostate cancer, oesophageal cancer, squamous cancer and non-small cell lung carcinomas.

It is contemplated that compounds and compositions provided herein may be used for the prevention or treatment of any disease state or condition mediated by a cyclin dependent kinase (CDK) and/or glycogen synthase kinase-3 (GSK-3). As used herein, the expression "disease state or condition mediated by a cyclin dependent kinase (CDK) and/or glycogen synthase kinase-3 (GSK-3)" refers to any disease or condition mentioned herein for which inhibition or modulation of a CDK and/or GSK-3 would be expected to provide a therapeutic or prophylactic benefit in a subject in need thereof.

In some embodiments, the active compound or composition is administered to a subject in need thereof (for example, a human or animal patient) in an amount sufficient to achieve the desired therapeutic effect. Compounds and compositions are typically administered in amounts that are therapeutically or prophylactically useful and which generally are non-toxic. However, in certain situations (for example in the case of life threatening diseases), the benefits of administering a compound or composition may outweigh the disadvantages of any toxic effects or side effects, in which case it may be considered desirable to administer compounds in amounts that are associated with a degree of toxicity.

A typical daily dose of a compound can be in the range from 100 picograms to 100 milligrams per kilogram of body weight, more typically 5 nanograms to 25 milligrams per kilogram of bodyweight, and more usually 10 nanograms to 15 milligrams per kilogram (e.g., 10 nanograms to 10 milligrams) per kilogram of bodyweight, although higher or lower doses may be administered where required. Ultimately, the quantity of compound administered and the type of composition used will be commensurate with the nature of the disease or physiological condition being treated and will be at the discretion of the physician.

Compounds and compositions provided herein can be administered as the sole therapeutic agent or they can be administered in combination therapy with one of more other compounds for treatment of a particular disease state, for example a neoplastic disease such as a cancer. Examples of other therapeutic agents that may be administered together (whether concurrently or at different time intervals) with the compounds and compositions provided herein include but are not limited to: topoisomerase inhibitors, alkylating agents, antimetabolites, DNA binders and microtubule inhibitors (tubulin targeting agents), such as cisplatin, cyclophosphamide, doxorubicin, irinotecan, fludarabine, flavopiridol, SFU, taxanes, mitomycin C or other chemotherapeutic agents, immune checkpoint inhibitors, or radiotherapy. Alternatively, the compounds and compositions provided herein can be administered in a combination therapy with monoclonal antibodies or signal transduction inhibitors. Compounds and compositions may also be administered in combination with bone marrow transplantation, peripheral blood stem cell transplantation, or other types of transplantation therapy.

In some embodiments, compounds and compositions may be administered in combination with immune checkpoint inhibitors. The blockade of immune checkpoints, which results in the amplification of antigen-specific T cell responses, has been shown to be a promising approach in human cancer therapeutics. Non-limiting examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine Ata receptor A2aR); and Killer Inhibitory Receptors. Non-limiting examples of immune checkpoint inhibitors include ipulimumab, nivolumab and lambrolizumab.

In other embodiments, there are provided methods for treating cancer in a subject, comprising administering to the subject a therapeutically effective amount of at least compound or composition of the present disclosure and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). There is also provided the use of the compounds and compositions in combination with other agents known in the art (e.g., arsenic trioxide) and other chemotherapeutic agents that may be developed in the future.

In some embodiments drawn to methods of treating cancer, the administration of a therapeutically effective amount of a compound or composition in combination with at least one chemotherapeutic agent results in a cancer survival rate greater than the cancer survival rate observed by administering either agent alone. In further embodiments drawn to methods of treating cancer, the administration of a therapeutically effective amount of a compound or composition in combination with at least one chemotherapeutic agent results in a reduction of tumor size or a slowing of tumor growth greater than reduction of the tumor size or slowing of tumor growth observed by administration of either agent alone.

In further embodiments, there are provided methods for treating or preventing cancer in a subject, comprising administering to the subject a therapeutically effective amount of at least one CDK and/or GSK3 inhibitor compound or composition and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs).

In other embodiments, there are provided methods of augmenting the rejection of tumor cells in a subject comprising administering a compound or composition in conjunction with at least one chemotherapeutic agent and/or radiation therapy, wherein the resulting rejection of tumor cells is greater than that obtained by administering either the compound, the chemotherapeutic agent or the radiation therapy alone.

In further embodiments, there are provided methods for treating cancer in a subject, comprising administering to the subject a therapeutically effective amount of at least one CDK and/or GSK3 inhibitor and at least one immunomodulator other than a CDK inhibitor. It should be understood that, as used herein, a "CDK and/or GSK3 inhibitor" refers to compounds provided herein, e.g., a compound of Formula I, a compound of Table 1, or a pharmaceutically acceptable salt or ester thereof, and to pharmaceutical compositions thereof.

In some embodiments, there are provided methods of treating or preventing a disease state or condition mediated by a cyclin dependent kinase (CDK) and/or glycogen synthase kinase-3 (GSK-3) in a subject in need thereof, comprising administering a therapeutically effective amount of at least one CDK and/or GSK3 inhibitor or a pharmaceutical composition thereof to the subject, such that the CDK and/or GSK-3 associated disease, disorder or condition is treated or prevented in the subject.

For the case of CDK inhibitors combined with other therapies, the two or more treatments may be given in individually varying dose schedules and via different routes.

In some embodiments, there are provided methods of inhibition or modulation of a cyclin dependent kinase (CDK) and/or glycogen synthase kinase-3 (GSK-3) in a subject, comprising administering an effective amount of at least one CDK and/or GSK3 inhibitor or a pharmaceutical composition thereof to the subject, such that the CDK and/or GSK-3 is inhibited or modulated in the subject.

Where a compound or composition provided herein is administered in combination therapy with one, two, three, four or more other therapeutic agents (preferably one or two, more preferably one), the compounds can be administered simultaneously or sequentially. When administered sequentially, they can be administered at closely spaced intervals (for example, over a period of 5-10 minutes) or at longer intervals (for example, 1, 2, 3, 4 or more hours apart, or even longer periods apart where required), the precise dosage regimen being commensurate with the properties of the therapeutic agent(s).

Compounds and compositions provided herein may also be administered in conjunction with non-chemotherapeutic treatments such as, without limitation, radiotherapy, photodynamic therapy, gene therapy, surgery, transplantation, immune checkpoint inhibitor therapy, and controlled diets.

Kits

There are also provided herein kits comprising a compound or composition of the present technology. Kits are generally in the form of a physical structure housing various components and may be used, for example, in practicing the methods provided herein. For example, a kit may include one or more compound disclosed herein (provided in, e.g., a sterile container), which may be in the form of a pharmaceutical composition suitable for administration to a subject. The compound can be provided in a form that is ready for use (e.g., a tablet or capsule) or in a form requiring, for example, reconstitution or dilution (e.g., a powder) prior to administration. When the compounds are in a form that needs to be reconstituted or diluted by a user, the kit may also include diluents (e.g., sterile water), buffers, pharmaceutically acceptable excipients, and the like, packaged with or separately from the compounds. When combination therapy is contemplated, the kit may contain several therapeutic agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may also contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1: Preparation of tert-butyl 4-(4-(2,6-dichlorobenzamido)-1H-pyrazole-3-carboxamido)piperidine-1-carboxylate (Compound A)

tert-Butyl 4-(4-amino-1H-pyrazole-3-carboxamido)piperidine-1-carboxylate (0.6 g, 1.98 mmol, 1.0 eq.) was dissolved in DMF (10 mL), Et$_3$N (404 mg, 4.0 mmol, 2.0 eq.) was added, then 2,6-dichlorobenzoyl chloride (490 mg, 2.3 mmol, 1.2 eq.) was added dropwise, The mixture was stirred at room temperature for 12 h under N$_2$ atmosphere, then the mixture was concentrated under reduced pressure. The residual material was purified by flash column chromatography (silica-gel; eluent, PE:EA, 1:2 to 1:1) to afford compound A (720 mg, 75%): $^1$H NMR (CD$_3$OD, 500 MHz) δ ppm 1.44-1.53 (m, 11H), 1.90 (d, J=10 Hz, 2H), 2.91 (s, 2H), 3.99-4.09 (m, 3H), 4.6 (s, 1H), 7.41-7.53 (m, 3H), 8.33 (s, 1H); $^{13}$C NMR (CD$_3$OD, 125 MHz): δ ppm 37.57, 40.50, 55.32, 88.13, 130.18, 130.99, 137.92, 140.74, 141.38, 142.37, 144.85, 163.36, 169.77, 172.07; m/z (ESI$^-$) 480.0 (M−H).

Example 2: Preparation of 4-(2,6-dichlorobenzamido)-N-(1-(4-((2-oxo-1,2,3,4-tetrahydroquinolin-7-yl)oxy)butyl)piperidin-4-yl)-1H-pyrazole-3-carboxamide (Compound 2)

4-(2,6-Dichlorobenzamido)-N-(piperidin-4-yl)-1H-pyrazole-3-carboxamide methanesulfonate (240 mg, 0.5 mmol, 1.0 eq.) was dissolved in DMF (10 mL), Et$_3$N (101 mg, 1.0 mmol, 2.0 eq.) was added, followed by dropwise addition of 7-(4-bromobutoxy)-3,4-dihydro-2(1H)-quinolinone (163 mg, 0.55 mmol, 1.1 eq.). The mixture was stirred at room temperature for 12 h under N$_2$ atmosphere, and then concentrated under reduced pressure. The residual material was purified by flash column chromatography (silica-gel; eluent: MeOH:DCM, 1:30 to 1:20), affording compound 2 (120 mg, 40%): $^1$H NMR (DMSO-d$_6$, 500 MHz) δ ppm 1.51-1.54 (m, 2H), 1.60-1.70 (m, 6H), 1.88 (t, J=10 Hz, 2H), 2.28 (t, J=5 Hz, 2H), 2.40 (t, J=5 Hz, 2H), 2.77 (t, J=5 Hz, 2H), 2.83 (d, J=10 Hz, 2H), 3.70 (s, 1H), 3.89 (t, J=5 Hz, 2H), 6.42 (s, 1H), 6.47 (dd, J=10 Hz, 5 Hz, 1H), 7.03 (d, J=10 Hz, 1H), 7.51-7.54 (m, 1H), 7.58 (d, J=5 Hz, 2H), 8.27 (s, 1H), 8.34 (s, 1H), 9.95 (s, 1H), 10.17 (s, 1H), 13.39 (s, 1H); $^{13}$C NMR (DMSO-d$_6$, 125 MHz) δ ppm 23.09, 24.00, 26.67, 30.76, 31.29, 46.32, 52.38, 57.42, 67.31, 101.70, 107.55, 115.43, 121.48, 128.36, 128.41, 131.25, 131.86, 132.71, 135.37, 139.17, 157.87, 160.31, 162.47, 170.26; m/z (ESI$^-$) 599.1 (M+H).

Example 3: Preparation of 4-(2,6-dichlorobenzamido)-N-(1-(L-valyl)piperidin-4-yl)-1H-pyrazole-3-carboxamide hydrochloride (Compound 3)

4-(2,6-Dichlorobenzamido)-N-(piperidin-4-yl)-1H-pyrazole-3-carboxamide methanesulfonate (480 mg, 1.0 mmol, 1.0 eq.) was dissolved in a mixture of DMF (7 mL) and Et$_3$N (220 mg, 2.0 mmol, 2.0 eq.), followed by addition of 2,5-dioxopyrrolidin-1-yl N-(tert-butoxycarbonyl)-L-valinate (320 mg, 1.0 mmol, 1.0 eq.). The mixture was stirred at room temperature for 12 h under N$_2$ atmosphere, and then concentrated under reduced pressure. The residual material was purified by flash column chromatography (silica-gel; eluent: PE:EA, 1:1), giving 4-(2,6-dichlorobenzamido)-N-(1-(N-Boc-L-valyl)piperidin-4-yl)-1H-pyrazole-3-carboxamide (516 mg, 89%). The above obtained 4-(2,6-dichlorobenzamido)-N-(1-(L-valyl)piperidin-4-yl)-1H-pyrazole-3-carboxamide (516 mg, 0.9 mmol, 1.0 eq.) was dissolved in dioxane (5 mL), followed by addition of 4 M HCl in dioxane (2 mL) dropwise. The mixture was stirred at room temperature for 5 h, followed by concentration under reduced pressure. The residual material was purified by flash column chromatography (silica-gel; eluent: DCM and MeOH, 20:1), affording compound 3 (210 mg, 45%): $^1$H NMR (D$_2$O, 500 MHz) δ ppm 0.98 (t, J=4 Hz, 3H), 1.08 (dd, J=8 Hz, 4 Hz, 3H), 1.55-1.61 (m, 2H), 2.03-2.07 (m, 2H), 2.22 (s, 1H), 3.01 (t, J=8 Hz, 1H), 3.35 (s, 1H), 3.94 (s, 1H), 4.09 (s, 1H), 4.36 (dd, J=12 Hz, 4 Hz, 2H), 7.47 (s, 3H), 8.30 (d, J=8 Hz, 1H); $^{13}$C NMR (D$_2$O, 125 MHz) δ ppm 15.75, 18.10, 29.37, 30.49, 31.17, 41.50, 44.67, 45.94, 55.41, 119.80, 123.28, 128.18, 131.46, 131.87, 133.82, 134.26, 163.02, 164.29, 167.88; m/z (ESI$^-$) 480.8 (M+H).

Example 4: Preparation of 4-(2,6-dichlorobenzamido)-N-(piperidin-4-yl)-1H-1-(dodecyloxymethyl)pyrazole-3-carboxamide hydrochloride (Compound 4)

Dodecanoic acid (2.0 g, 10.0 mmol, 1.0 eq.) was dissolved in DCM–H$_2$O (1:1, 40 mL), followed by addition of chloromethyl sulfurochloridate (1.2 mL, 11.5 mmol, 1.15 eq.), Na$_2$CO$_3$ (4.1 g, 40 mmol, 4.0 eq) and TBAB (320 mg, 1.0 mmol, 0.1 eq.), subsequently. The mixture was stirred at room temperature for 12 h, diluted with DCM (100 mL) and H$_2$O (100 mL). The organic layer was separated, washed with brine (50 mL), and concentrated under reduced pressure. The residual material was purified by flash column chromatography (silica-gel; eluent: pet-ether), giving chloromethyl dodecanoate (2.0 g, 80%). Compound A (530 mg, 1.1 mmol, 1.0 eq.) was dissolved in CH$_3$CN (10 mL), followed by addition of chloromethyl dodecanoate (273 mg, 1.1 mmol, 1.0 eq.) and NaHCO$_3$ (185 mg, 2.2 mmol, 2.0 eq), subsequently. The mixture was stirred for 48 h under nitrogen and heated to 60° C., and then concentrated under reduced pressure. The residual material was purified by flash column chromatography (silica-gel; eluent: PE:EA, 2:1) to afford tert-butyl 4-(4-(2,6-dichlorobenzamido)-1-((dodecanoyloxy)methyl)-1H-pyrazole-3-carboxamido) piperidine-1-carboxylate (190 mg, 25%): $^1$H NMR (CDCl$_3$, 500 MHz) δ ppm 0.81 (t, J=10 Hz, 3H), 1.18-1.21 (m, 18H), 1.39 (s, 9H), 1.51-1.60 (m, 2H), 1.89 (d, J=5 Hz, 2H), 2.30 (t, J=10 Hz, 2H), 2.80 (t, J=10 Hz, 2H), 3.95-4.03 (m, 3H), 5.94 (s, 2H), 6.76 (d, J=5 Hz, 1H), 7.20-7.28 (m, 3H), 8.50 (s, 1H), 9.77 (s, 1H). The above obtained compound (190 mg, 0.3 mmol, 1.0 eq.) was dissolved in dioxane (10 mL), followed by addition of 4 M HCl in dioxane (4 mL). The mixture was stirred at room temperature for 12 h and then concentrated under reduced pressure. The residual material was purified by flash column chromatography (silica-gel; eluent: DCM:MeOH, 20:1), giving compound 4 (120 mg, 40%): $^1$H NMR (CD$_3$OD, 500 MHz): δ ppm 0.87 (t, J=8 Hz, 3H), 1.25 (s, 16H), 1.60 (s, 2H). 1.91 (dd, J=12 Hz, 4 Hz, 2H), 2.13 (d, J=8 Hz, 2H), 2.38 (t, J=8 Hz, 2H), 3.10 (t, J=8 Hz, 2H), 3.43 (d, J=8 Hz, 2H), 4.12 (t, J=8 Hz, 1H), 6.13 (s, 2H), 7.47 (s, 3H), 8.55 (s, 1H); $^{13}$C NMR (CD$_3$OD, 125 MHz): δ ppm 14.47, 23.69, 25.74, 29.42, 29.94, 30.31, 30.41, 30.56, 30.68, 33.02, 34.63, 44.27, 45.30, 73.93, 124.01, 125.27, 129.48, 132.89, 133.34, 135.61, 136.38, 163.16, 164.12, 174.30; m/z (ESI$^+$) 594.1 (M+H).

Example 5: Preparation of 4-(2,6-dichlorobenzamido)-N-(1-(N-glycyl-L-valy)piperidin-4-yl)-1H-pyrazole-3-carboxamide hydrochloride (Compound 5)

N-(tert-Butoxycarbonyl)glycyl-L-valine (274 mg, 1.0 mmol, 1.0 eq.) and Et$_3$N (202 mg, 2.0 mmol, 2.0 eq.) were added to a solution of 4-(2,6-dichlorobenzamido)-N-(piperidin-4-yl)-1H-pyrazole-3-carboxamide hydrochloride (417 mg, 1.0 mmol, 1.0 eq.) in DMF (10 mL), followed by addition of HATU (418 mg, 1.1 mmol, 1.1 eq.). The mixture was stirred at room temperature for 12 h, and then concentrated under reduced pressure. The residual material was purified by flash column chromatography (silica-gel; eluent, ethyl acetate), giving 4-(2,6-dichlorobenzamido)-N-(1-(N—(N-'Boc-glycyl)-L-valyl)piperidin-4-yl)-1H-pyrazole-3-carboxamide (500 mg, 78%). The material thus obtained (500 mg, 1.27 mmol, 1.0 eq.) was dissolved in dioxane (10 mL), followed by addition of 4M HCl in dioxane (5 mL). The mixture was stirred at room temperature for 12 h, and then concentrated under reduced pressure. The residual material was purified by flash column chromatography (silica-gel; eluent: DCM:MeOH, 20:1), affording compound 5 (100 mg, 14%): $^1$H NMR (D$_2$O, 500 MHz) δ ppm 0.92-0.97 (m, 6H), 1.50 (s, 1H), 1.66 (d, J=8 Hz, 1H), 2.05-2.09 (m, 3H), 2.96 (s, 1H), 3.35 (s, 1H), 3.84-3.94 (m, 2H), 4.10 (t, J=12 Hz, 2H), 4.35 (d, J=12 Hz, 1H), 4.79 (s, 1H), 7.46 (s, 3H), 8.30

(d, J=8 Hz, 1H); $^{13}$C NMR (CD$_3$OD, 125 MHz) δ ppm 18.15, 19.84, 31.75, 32.30, 33.09, 41.47, 42.32, 45.95, 47.39, 55.66, 122.70, 122.83, 129.38, 132.76, 133.21, 134.15, 136.41, 163.13, 164.43, 167.15, 171.41; m/z (ESI$^+$) 537.9 (M+H).

Example 6: Preparation of 4-(2,6-dichlorobenzamido)-N-(1-(3-methylbutanoyl)piperidin-4-yl)-1H-pyrazole-3-carboxamide (Compound 6)

Et$_3$N (202 mg, 2.0 mmol, 2.0 eq) and 3-methylbutanoic acid (102 mg, 1.0 mmol, 1.0 eq.) were added to a solution of 4-(2,6-dichlorobenzamido)-N-(piperidin-4-yl)-1H-pyrazole-3-carboxamide hydrochloride (417 mg, 1.0 mmol, 1.0 eq.) in DMF (10 mL), followed by addition of HATU (418 mg, 1.1 mmol, 1.1 eq.). The mixture was stirred at room temperature for 12 h, and then concentrated under reduced pressure. The residual material was purified by flash column chromatography (silica-gel; eluent: PE:EA, 2:1), affording compound 6 (380 mg, 82%): $^1$H NMR (CD$_3$OD, 500 MHz) δ ppm 0.97 (dd, J=10 Hz, 5 Hz, 6H), 1.52-1.56 (m, 2H), 1.93-2.07 (m, 3H), 2.29 (d, J=10 Hz, 2H), 2.80 (t, J=15 Hz, 1H), 3.21 (t, J=15 Hz, 1H), 3.99 (d, J=15 Hz, 1H), 4.08-4.12 (m, 1H), 4.52 (d, J=15 Hz, 1H), 7.46-7.52 (m, 3H), 8.35 (s, 1H); $^{13}$C NMR (CD$_3$OD, 125 MHz) δ ppm 23.02, 23.12, 27.30, 32.60, 33.47, 42.02, 43.09, 46.24, 47.78, 122.49, 123.16, 129.64, 132.94, 133.62, 134.70, 136.85, 163.42, 164.99, 173.56; m/z (ESI$^+$) 466.0 (M+H).

Example 7: Preparation of 4-(2,6-dichlorobenzamido)-N-(1-(L-valyl-glycyl)piperidin-4-yl)-1H-pyrazole-3-carboxamide hydrochloride (Compound 7)

4-(2,6-Dichlorobenzamido)-N-(piperidin-4-yl)-1H-pyrazole-3-carboxamide hydrochloride (417 mg, 1.0 mmol, 1.0 eq.) and N-(tert-butoxycarbonyl)-L-valyl-glycine (274 mg, 1.0 mmol, 1.0 eq.) were dissolved in DMF (10 mL). To the mixture were added Et$_3$N (202 mg, 2.0 mmol, 2.0 eq.) and HATU (418 mg, 1.1 mmol, 1.1 eq). The mixture was stirred at room temperature for 12 h, concentrated under reduced pressure. The residual material was purified by flash column chromatography (silica-gel; eluent: PE:EA, 1:1), giving 4-(2,6-dichlorobenzamido)-N-(1-(N-Boc-L-valyl-glycyl)piperidin-4-yl)-1H-pyrazole-3-carboxamide (560 mg, 88%). The compound thus obtained (560 mg, 0.88 mmol, 1.0 eq.) was dissolved in dioxane (5 mL), followed by addition of 4M HCl in dioxane (5 mL). The mixture was stirred at room temperature for 12 h, and concentrated under reduced pressure. The residual material was purified by flash column chromatography (silica-gel; eluent: DCM:MeOH, 20:1), affording compound 7 (230 mg, 50%): $^1$H NMR (CD$_3$OD, 500 MHz) δ ppm 1.08 (d, J=10 Hz, 6H), 1.50-1.69 (m, 2H), 1.95-2.05 (m, 2H), 2.17-2.25 (m, 1H), 2.88 (t, J=15 Hz, 1H), 3.23 (t, J=15 Hz, 1H), 3.71 (d, J=10 Hz, 1H), 3.90 (d, J=15 Hz, 1H), 4.08-4.26 (m, 3H), 4.46 (d, J=15 Hz, 1H), 7.44-7.52 (m, 3H), 8.34 (s, 1H); $^{13}$C NMR (D$_2$O, 125 MHz) δ ppm 17.09, 17.67, 29.99, 30.63, 31.17, 40.93, 41.45, 43.65, 46.09, 58.79, 120.51, 122.98, 128.30, 131.62, 131.86, 133.89, 134.11, 162.99, 163.64, 167.70, 169.62; m/z (ESI$^+$) 538.0 (M+H).

Example 8: Preparation of 4-(2,6-dichlorobenzamido)-N-(1-Boc-piperidin-4-yl)-1-dodecanoyl-1H-pyrazole-3-carboxamide (Compound 8)

Compound A (481 mg, 1.0 mmol, 1.0 eq.) and Et$_3$N (202 mg, 2.0 mmol, 2.0 eq.) were dissolved in DMF (10 mL), then dodecanoyl chloride (219 mg, 1.0 mmol, 1.0 eq.) was added. The contents were stirred for 12 h under Nitrogen. The mixture was concentrated under reduced pressure. The residual material was purified by flash column chromategraphy (silica-gel; eluent: PE:EA, 3:1), affording compound 8 (300 mg, 45%): $^1$H NMR (DMSO-d$_6$, 500 MHz) δ ppm 0.9 (t, J=10 Hz, 3H), 1.29-1.40 (m, 25H), 1.55-1.59 (m, 2H), 1.75-1.81 (m, 2H), 1.87-1.91 (m, 2H), 2.85 (s, 2H), 3.23 (t, J=10 Hz, 2H), 4.06-4.12 (m, 3H), 7.45-7.52 (m, 3H), 8.91 (s, 1H); $^{13}$C NMR (DMSO-d$_6$, 125 MHz) δ ppm 14.49, 23.72, 25.20, 28.73, 30.10, 30.45, 30.60, 30.71, 32.46, 33.04, 34.12, 48.07, 81.13, 120.44, 125.23, 129.50, 132.93, 133.31, 136.23, 138.76, 156.33, 163.33, 163.49, 173.21; m/z (ESI$^-$) 662.2 (M−H).

Example 9: Preparation of 4-(2,6-dichlorobenzamido)-N-(piperidin-4-yl)-1-(L-valyloxymethyl)-1H-pyrazole-3-carboxamide dihydrochloride (Compound 10)

(tert-Butoxycarbonyl)-L-valine (434 mg, 2.0 mmol, 1.0 eq.) was dissolved in DCM–H$_2$O (v/v, 1:1, 10 mL), followed by addition of chloromethyl sulfurochloridate (0.24 mL, 2.3 mmol, 1.15 eq.), Na$_2$CO$_3$ (850 mg, 8.0 mmol, 4.0 eq.), and TBAB (65 mg, 0.2 mmol, 0.1 eq.), subsequently. The mixture was stirred at room temperature for 12 h, diluted with DCM (50 mL) and H$_2$O (50 mL). The organic layer was separated, washed with brine (3×20 mL), and concentrated under reduced pressure. The residual material was purified by flash column chromatography (silica-gel; eluent, pet-ether), giving chloromethyl N-(tert-butoxycarbonyl)-L-valinate (480 mg, 90.5%). Compound A (481 mg, 1.0 mmol, 1.0 eq.) was dissolved in CH$_3$CN (10 mL), followed by addition of chloromethyl N-(tert-butoxycarbonyl)-L-valinate (265 mg, 1.0 mmol, 1.0 eq.) and NaHCO$_3$ (168 mg, 2.0 mmol, 2.0 eq.), subsequently. The mixture was stirred for 48 h under nitrogen at 60° C. The mixture was concentrated under reduced pressure. The residual material was purified by flash column chromatography (silica-gel; eluent: PE:EA, 2:1), giving 4-(2,6-dichlorobenzamido)-N-(piperidin-4-yl)-1-(N-Boc-L-valyloxymethyl)-1H-pyrazole-3-carboxamide (450 mg, 63%). This Boc-protected compound (240 mg, 0.5 mmol, 1.0 eq.) was dissolved in dioxane (10 mL), followed by addition of 4M HCl in dioxane (0.5 mL). The mixture was stirred at room temperature for 12 h and concentrated under reduced pressure. The residual material was purified by flash column chromatography (silica-gel; eluent: DCM:MeOH, 20:1), affording compound 10 (120 mg, 47%): $^1$H NMR (D$_2$O, 500 MHz) δ ppm 0.93 (t, J=10 Hz, 6H), 1.82-1.91 (m, 2H), 2.22 (d, J=10 Hz, 2H), 2.30-2.36 (m, 1H), 3.18 (t, J=10 Hz, 2H), 3.52 (d, J=10 Hz, 2H), 4.12-4.15 (m, 2H), 6.24 (d, J=10 Hz, 1H), 6.47 (d, J=10 Hz, 1H), 7.47-7.54 (m, 3H), 8.58 (s, 1H); $^{13}$C NMR (D$_2$O, 125 MHz) δ ppm 16.91, 27.79, 29.35, 42.91, 44.21, 57.94, 73.75, 120.78, 126.71, 128.30, 128.48, 131.51, 132.17, 133.72, 162.66, 165.30, 168.91; m/z (ESI$^+$) 511.1 (M+H).

Example 10: Synthesis of Sodium (4-(2,6-dichlorobenzamido)-3-(piperidin-4-ylcarbamoyl)-1H-pyrazole-1-methyl phosphate disodium Salt (Compound 11)

Compound A (481 mg, 1.0 mmol, 1.0 eq.) and di-tert-butyl (chloromethyl) phosphate (258.7 mg, 1.0 mmol, 1.0 eq.) were dissolved in AcNMe$_2$ (10 mL), followed by addition of Cs$_2$CO$_3$ (652 mg, 2.0 mmol, 2.0 eq.). The mixture was stirred for 12 h under nitrogen at 40 to 45° C.

The mixture was diluted with DCM (50 mL) and H$_2$O (50 mL). The organic layer was separated, washed with brine (3×20 mL), and concentrated under reduced pressure. The residual material was purified by flash column chromatography (silica-gel; eluent: PE:Acetone, 3:1), giving di-tert-butyl (4-(2,6-dichlorobenzamido)-3-(piperidin-4-ylcarbamoyl)-1H-pyrazol-1-methyl phosphate (240 mg, 34.1%). The phosphate ester thus obtained (150 mg, 0.2 mmol, 1.0 eq.) was dissolved in DCM (2 mL), followed by addition of CF$_3$COOH (1 mL). The mixture was stirred for 1 min, concentrated under reduced pressure, and treated with t-BuOMe (5 mL). Solid material was collected by filtration and dried, giving (4-(2,6-dichlorobenzamido)-3-(piperidin-4-ylcarbamoyl)-1H-pyrazol-1-yl)methyl dihydrogen phosphate (75 mg, 76.2%). This (4-(2,6-dichlorobenzamido)-3-(piperidin-4-ylcarbamoyl)-1H-pyrazol-1-yl)methyl dihydrogen phosphate (49.1 mg, 0.1 mmol, 1.0 eq.) was dissolved in H$_2$O (2 mL) and treated with NaOH (8 mg, 0.2 mmol, 2.0 eq.). The mixture were stirred for 0.5 h and lyophilized, affording compound 11 (47 mg, 87.9%): $^1$H NMR (500 MHz, D$_2$O) δ ppm 1.53 (d, J=10.5 Hz, 2H), 1.94 (d, J=12.8 Hz, 2H), 2.72 (t, J=12.2 Hz, 2H), 3.07 (d, J=12.2 Hz, 2H), 3.90 (s, 1H), 5.66 (d, J=7.5 Hz, 2H), 7.37 (d, J=8.4 Hz, 1H), 7.43 (d, J=8.0 Hz, 2H), 8.32 (s, 1H); $^{13}$C NMR (125 MHz, D$_2$O) δ ppm 30.30, 43.26, 45.70, 75.70, 123.45, 125.10, 128.18, 131.30, 131.44, 135.57, 136.54, 163.00, 165.66; m/z (ESI$^+$) 491.8 (M+H).

Example 11: Preparation of N-((4-(4-(2,6-dichlorobenzamido)-1H-pyrazole-3-carboxamido)-1-piperidinyl)(phenoxy)phosphinyl)-L-alanine methyl Ester (Compound 12)

Phenyl phosphorodichloridate (4.0 g, 18.96 mmol, 1.0 eq.), L-alanine methyl ester hydrochloride (2.64 g, 18.96 mmol, 1.0 eq.) were dissolved in DCM (40 mL). To the mixture at −78 to −70° C., Et$_3$N (3.83 g, 37.92 mmol, 2.0 eq.) was added dropwise. The mixture was stirred for 1 h under nitrogen, and then concentrated under reduced pressure. The residual material was purified by flash column chromatography (silica-gel; eluent: PE:EA, 3:1), giving N-(chloro(phenoxy)phosphinyl)-L-alanine methyl ester (2.0 g, 38.1%): $^1$H NMR (CDCl$_3$, 500 MHz) δ ppm 1.52-1.57 (m, 3H), 3.78-3.85 (m, 3H), 4.16-4.26 (m, 2H), 7.30 (d, J=10 Hz, 3H), 7.36-7.44 (m, 2H). 4-(2,6-Dichlorobenzamido)-N-(piperidin-4-yl)-1H-pyrazole-3-carboxamide hydrochloride (208 mg, 0.5 mmol, 1.0 eq.) and (chloro(phenoxy)phosphinyl)-L-alanine methyl ester (140 mg, 0.5 mmol, 1.0 eq.) were dissolved in DCM (5 mL), followed by addition of Et$_3$N (101 mg, 1.0 mmol, 2.0 eq.). The mixture was stirred for 12 h under nitrogen, and then concentrated under reduced pressure. The residual material was purified by flash column chromatography (silica-gel; eluent: PE:EA, 2:1), giving compound 12 (120 mg, 38.5%): $^1$H NMR (CD$_3$OD, 500 MHz) δ ppm 1.39 (dd, J=15 Hz, 10 Hz, 3H), 1.52-1.57 (m, 2H), 1.86-1.90 (m, 2H), 2.82-2.89 (m, 2H), 3.72 (d, J=10 Hz, 6H), 3.93-3.96 (m, 2H), 4.64 (s, 1H), 7.15-7.22 (m, 3H), 7.34-7.37 (m, 2H), 7.45-7.51 (m, 3H), 8.35 (s, 1H); m/z (ESI$^+$) 622.9 (M+H).

Example 12: Preparation of 4-(2,6-dichlorobenzamido)-N-(1-(2-oxido-4H-benzo[d][1,3,2]dioxaphosphinin-2-yl)piperidin-4-yl)-1H-pyrazole-3-carboxamide (Compound 13)

2-(Hydroxymethyl)phenol (2.0 g, 16.1 mmol, 1.0 eq.) and POCl$_3$ (2.7 g, 17.7 mmol, 1.1 eq.) were dissolved in THF (40 mL), followed by addition of Et$_3$N (3.4 g, 35.8 mmol, 2.1 eq.) dropwise while the system was cooled to −78 and −70° C. The mixture was stirred for 1 h under nitrogen and then concentrated under reduced pressure. The residual material was purified by flash column chromatography (silica-gel; eluent: PE:EA, 3:1) to afford 2-chloro-2-oxo-4H-1,3,2-benzodioxaphosphinine (2.3 g, 70.0%): $^1$H NMR (CDCl$_3$, 500 MHz): δ ppm 5.51-5.57 (m, 2H), 7.13-3.16 (m, 2H), 7.25-7.29 (m, 1H), 7.39-7.43 (m, 1H). 4-(2,6-Dichlorobenzamido)-N-(piperidin-4-yl)-1H-pyrazole-3-carboxamide hydrochloride (417 mg, 1.0 mmol, 1.0 eq.) and 2-chloro-2-oxo-4H-1,3,2-benzodioxaphosphinine (204 mg, 1.0 mmol, 1.0 eq.) were dissolved in DCM (10 mL), followed by addition of Et$_3$N (202 mg, 2.0 mmol, 2.0 eq.). The mixture was stirred for 12 h under nitrogen. The mixture was concentrated under reduced pressure, and the residual material was purified by flash column chromatography (silica-gel; eluent: PE:EA, 1:1), giving compound 13 (300 mg, 54.5%): $^1$H NMR (CD$_3$OD, 500 MHz) δ ppm 1.59-1.64 (m, 2H), 1.92 (d, J=10 Hz, 2H), 2.98 (t, J=15 Hz, 2H), 3.58 (s, 2H), 4.0-4.03 (m, 1H), 5.28-5.35 (m, 1H), 5.51-5.53 (m, 1H), 7.11-7.12 (m, 1H), 7.19 (d, J=10 Hz, 1H), 7.26 (d, J=10 Hz, 1H), 7.38 (s, 1H), 7.47-7.52 (m, 3H), 8.36 (s, 1H); $^{13}$C NMR (CD$_3$OD, 125 MHz) δ ppm 32.96, 44.83, 47.44, 68.53, 119.20, 122.59, 123.01, 123.26, 125.30, 126.97, 129.48, 130.96, 132.78, 133.45, 134.42, 136.68, 152.47, 163.29, 164.66; m/z (ESI$^+$) 549.8 (M+H).

Example 13: Synthesis of N-((4-(4-(2,6-dichlorobenzamido)-1H-pyrazole-3-carboxamido)piperidin-1-yl)(naphthalen-1-yloxy)phosphinyl)-L-alanine methyl Ester (Compound 16)

1-Naphthol (0.72 g, 4.99 mmol, 1.0 eq.) and phosphorus oxychloride (767 mg, 4.99 mmol, 1.0 eq.) were suspended in anhydrous ether (20 mL), and the temperature was cooled to −78° C. Triethylamine (505 mg, 4.99 mmol, 1.0 eq.) was added dropwise to the mixture, and the reaction mixture was stirred at −78° C. for 0.5 h. The reaction mixture was warmed up to r.t. and stirred at r.t. overnight. The mixture was filtered, and the filtrate was concentrated to give crude 1-naphthyl phosphorodichloridate as light yellow oil (1.1 g, 85.0%), which was used without purification. To a stirred solution of 1-naphthyl phosphorodichloridate (1.1 g, 4.2 mmol, 1.0 eq.) and L-alanine methyl ester hydrochloride (586 mg, 4.2 mmol, 1.0 eq.) in anhydrous DCM (30 mL) was added dropwise anhydrous TEA (848 mg, 8.4 mmol, 2.0 eq.) at −78° C. under nitrogen. The reaction mixture was stirred at −78° C. for 1 h and then at room temperature for 1 h. The solvent was removed under reduced pressure and the residue was purified by flash column chromatography (silica-gel; eluting: PE:EA, 1:1), giving N-(chloro(1-naphthyloxy)phosphinyl)-L-alanine methyl ester (790 mg, 57.4%). To a stirred solution of the 4-(2,6-dichlorobenzamido)-N-(piperidin-4-yl)-1H-pyrazole-3-carboxamide hydrochloride (410 mg, 0.98 mmol, 1.1 eq.) and TEA (198 mg, 1.96 mmol, 2.2 eq.) in anhydrous DCM (10 mL) was added dropwise, at 0° C. under nitrogen, N-(chloro(1-naphthyloxy)phosphinyl)-L-alanine methyl ester (289 mg, 0.88 mmol, 1.0 eq.). The reaction mixture was stirred at room temperature for 5 h. The solvent was removed under reduced pressure and the residue was purified by flash column chromatography (silica-gel; eluent: DCM:MeOH, 20:1), affording compound 16 (226 mg, 38.1%): $^1$H NMR (500 MHz, CD$_3$OD) δ ppm 1.59-1.32 (m, 5H), 1.81 (s, 2H), 2.81 (d, J=23.5 Hz, 2H), 3.81-3.64 (m, 5H), 3.87 (s, 1H), 4.00 (s, 1H), 7.59-7.32 (m, 7H), 7.66 (s, 1H), 7.86 (d, J=6.8 Hz, 1H), 8.17 (dd, J=15.0, 7.9 Hz, 1H), 8.31 (s, 1H); $^{13}$C NMR (125 MHz, CD$_3$OD) δ ppm 20.68, 33.01, 45.18, 47.65, 51.02, 52.71, 115.90, 122.32, 122.63, 122.72, 122.96, 125.39, 125.49, 126.56, 127.31, 127.68, 128.87, 129.43, 132.73, 133.40, 134.49, 136.27, 136.62, 148.32, 163.20, 164.62, 175.83; m/z (ESI$^-$) 670.7 (M−H).

Example 14: Preparation of N-((4-(4-(2,6-dichlorobenzamido)-1H-pyrazole-3-carboxamido)piperidin-1-yl)(naphthalen-1-yloxy)phosphinyl)-L-alanine isopropyl Ester (Compound 17)

4-(2,6-dichlorobenzamido)-N-(piperidin-4-yl)-1H-pyrazole-3-carboxamide hydrochloride (417 mg, 1.0 mmol, 1.0 eq.) and N-(chloro(1-naphthyloxy)phosphinyl)-L-alanine isopropyl ester (356 mg, 1.0 mmol, 1.0 eq.) were dissolved in DCM (15 mL), followed by addition of Et$_3$N (303 mg, 3.0 mmol, 2.0 eq.). The mixture was stirred for 12 h under nitrogen, and then concentrated under reduced pressure. The residual material was purified by flash column chromatography (silica-gel; eluent: DCM:MeOH, 30:1), affording compound 17 (200 mg, 29%): $^1$H NMR (CD$_3$OD, 500 MHz) δ ppm 1.21-1.37 (m, 6H), 1.40-1.44 (m, 4H), 1.53 (t, J=10 Hz, 1H), 1.85 (s, 2H), 2.86 (s, 2H), 3.78 (s, 2H), 3.88-4.0 (m, 2H), 4.99-5.03 (m, 1H), 7.43-7.57 (m, 7H), 7.70 (s, 1H), 7.88 (s, 1H), 8.18-8.33 (m, 1H), 8.33 (s, 1H); $^{31}$P NMR (CD$_3$OD, 203 MHz): δ ppm 10.83, 11.40; m/z (ESI$^+$) 701.1 (M+H).

Example 15: Preparation of isopropyl ((4-(4-(2,6-dichlorobenzamido)-1H-pyrazole-3-carboxamido)piperidin-1-yl)(phenoxy)phosphoryl)-L-alaninate (Compound 18)

Phenyl phosphorodichloridate (2.0 g, 9.5 mmol, 1.0 eq.) and L-alanine isopropyl ester hydrochloride (1.6 g, 9.5 mmol, 1.0 eq.) were dissolved in DCM (20 mL). To the mixture was added Et$_3$N (1.9 g, 19 mmol, 2.0 eq.) dropwise at −78 to −70° C. The mixture was stirred for 1 h under nitrogen, and concentrated under reduced pressure. The residual material was purified by flash column chromatography (silica-gel; eluent: PE:EA, 3:1), affording N-(chloro(phenoxy)phosphinyl)-L-alanine isopropyl ester (1.9 g, 65.4%). 4-(2,6-Dichlorobenzamido)-N-(piperidin-4-yl)-1H-pyrazole-3-carboxamide hydrochloride (417 mg, 1.0 mmol, 1.0 eq.) and N-(chloro(phenoxy)phosphinyl)-L-alanine isopropyl ester (305 mg, 1.0 mmol, 1.0 eq.) were dissolved in DCM (10 mL), followed by addition of Et$_3$N (202 mg, 2.0 mmol, 2.0 eq.). The mixture was stirred for 12 h under nitrogen, and then concentrated under reduced pressure. The residual material was purified by flash column chromatography (silica-gel; eluent: PE:EA, 2:1), giving compound 18 (200 mg, 30.7%): $^1$H NMR (CD$_3$OD, 500 MHz) δ ppm 1.27-1.31 (m, 6H), 1.38-1.44 (m, 3H), 1.56 (d, J=15 Hz, 2H), 1.93 (s, 2H), 2.87 (s, 2H), 3.77 (s, 2H), 3.94-3.97 (m, 2H), 5.03-5.06 (m, 1H), 7.25-7.26 (m, 3H), 7.38-7.40 (m, 2H), 7.50-7.56 (m, 3H), 8.39 (s, 1H); $^{13}$C NMR (CD$_3$OD, 125 MHz) δ ppm 20.52, 21.82, 32.88, 44.84, 47.67, 51.06, 69.90, 121.31, 121.47, 122.41, 122.82, 125.53, 129.32, 130.52, 132.62, 133.30, 134.24, 136.52, 152.38, 163.12, 164.48, 174.72; m/z (ESI$^+$) 651.0 (M+H).

Example 16: Preparation of 4-(4-(2,6-dichlorobenzamido)-1H-pyrazole-3-carboxamido)piperidine-1-methanephosphonic acid disodium Salt (Compound 20)

4-(2,6-Dichlorobenzamido)-N-(piperidin-4-yl)-1H-pyrazole-3-carboxamide hydrochloride (1.04 g, 2.5 mmol, 1.0 eq.) and (diethoxyphosphoryl)methyl 4-methylbenzenesulfonate (0.81 g, 2.5 mmol, 1.0 eq.) were dissolved in DMF (10 mL), followed by addition of Et$_3$N (732 mg, 7.15 mmol, 3.0 eq.). The mixture was stirred for 12 h, and then concentrated under reduced pressure. The residual material was purified by flash column chromatography (silica-gel; eluent: DCM:MeOH, 10:1), giving 4-(4-(2,6-dichlorobenzamido)-1H-pyrazole-3-carboxamido)piperidine-1-methanephosphonic acid diethyl ester (320 mg, 24%). 4-(4-(2,6-Dichlorobenzamido)-1H-pyrazole-3-carboxamido)piperidine-1-methanephosphonic acid diethyl ester (300 mg, 0.56 mmol, 1.0 eq.) was dissolved in CH$_3$CN (5 mL), followed by addition of TMSBr (260 mg, 1.7 mmol, 3.0 eq.). The mixture was stirred for 36 h under nitrogen, diluted with MeOH (10 mL). The solid material was collected by filtration, and the filter cake was washed with MeOH (10 mL) and dried, affording 4-(4-(2,6-dichlorobenzamido)-1H-pyrazole-3-carboxamido)piperidine-1-methanephosphonic acid (100 mg, 38%). This phosphonic acid (100 mg, 0.21 mmol, 1.0 eq.) was dissolved in H$_2$O (5 mL), and treated with NaOH (16.8 mg, 0.42 mmol, 2.0 eq.). The mixture was stirred for 0.5 h and then lyophilized, giving compound 20 (100 mg, 92%): $^1$H NMR (CD$_3$OD, 500 MHz) δ ppm 1.31 (d, J=15 Hz, 1H), 1.67-1.75 (m, 2H), 1.90-1.93 (m, 2H), 2.39 (t, J=10 Hz, 2H), 2.58 (d, J=10 Hz, 2H), 3.27 (s, 1H), 3.84 (s, 1H), 7.41-7.49 (m, 3H), 8.26 (s, 1H); $^{13}$C NMR (CD$_3$OD, 125 MHz) δ ppm 32.29, 47.10, 55.32, 58.60, 59.72, 123.31, 124.30, 129.44, 132.59, 133.51, 134.16, 137.02, 163.30, 164.94; $^{31}$P NMR (CD$_3$OD, 203 MHz) δ ppm 13.86; m/z (ESI$^+$) 477.6 (M+H).

Example 17: Preparation of (4-(2,6-dichlorobenzamido)-3-(piperidin-4-ylcarbamoyl)-1H-pyrazol-1-yl)methyl isopropyl carbonate hydrochloride (Compound 25)

Compound A (481 mg, 1.0 mmol, 1.0 eq.) and chloromethyl isopropyl carbonate (304 mg, 2.0 mmol, 2.0 eq.) were dissolved in CH$_3$CN (10 mL), followed by addition of NaHCO$_3$ (168 mg, 2.0 mmol, 2.0 eq.). The mixture was stirred for 12 h under nitrogen at 25° C. and then concentrated under reduced pressure. The residual material was purified by flash column chromatography (silica-gel; eluent: PE:EA, 1:1), affording tert-butyl 4-(4-(2,6-dichlorobenzamido)-1-((isopropoxycarbonyloxy)methyl)-1H-pyrazole-3-carboxamido)piperidine-1-carboxylate (240 mg, 40.1%). The product thus obtained (240 mg, 0.4 mmol, 1.0 eq.) was dissolved in 1,4-dioxane (4 mL), followed by addition of 4M HCl in 1,4-dioxane (2 mL). The mixture was stirred for 12 h, and then concentrated under reduced pressure. The residual material was purified by flash column chromatography (silica-gel; eluent: DCM:MeOH, 20:1), affording compound 25 (100 mg, 46.7%): $^1$H NMR (D$_2$O, 500 MHz) δ ppm 1.26-1.28 (m, 6H), 1.79-1.87 (m, 2H), 2.17 (d, J=15 Hz, 2H), 3.14 (t, J=10 Hz, 2H), 3.50 (d, J=10 Hz, 2H), 4.03 (s, 1H), 4.89-4.94 (m, 1H), 6.13 (s, 2H), 7.41 (s, 3H), 8.53 (s, 1H); $^{13}$C NMR (D$_2$O, 125 MHz) δ ppm 20.72, 20.81, 27.72, 42.87, 44.02, 75.07, 120.84, 125.87, 128.25, 131.44, 132.08, 133.65, 136.14, 153.91, 162.50, 164.59; m/z (ESI$^+$) 497.8 (M+H).

Example 18: Preparation of 4-(2,6-dichlorobenzamido)-1-dodecanoyl-N-(piperidin-4-yl)-1H-pyrazole-3-carboxamide (Compound 27)

4-(2,6-Dichlorobenzamido)-N-(piperidin-4-yl)-1H-pyrazole-3-carboxamide hydrochloride (1.6 g, 3.8 mmol, 1.0 eq.)

and (9H-fluoren-9-yl)methyl carbonochloridate (1.0 g, 3.8 mmol, 1.0 eq.) were dissolved in dioxane-H$_2$O (20 mL, 1:1), followed by addition of NaHCO$_3$ (640 mg, 7.6 mmol, 2.0 eq.). The mixture was stirred for 12 h, and then concentrated under reduced pressure. The residual material was purified by flash column chromatography (silica-gel; eluent: PE:EA, 1:1), affording (9H-fluoren-9-yl)methyl 4-(4-(2,6-dichlorobenzamido)-1H-pyrazole-3-carboxamido)piperidine-1-carboxylate (1.0 g, 43.6%). (9H-fluoren-9-yl)methyl 4-(4-(2,6-dichlorobenzamido)-1H-pyrazole-3-carboxamido)piperidine-1-carboxylate (900 mg, 1.5 mmol, 1.0 eq.) and dodecanoyl chloride (358 mg, 1.64 mmol, 1.1 eq.) were dissolved in DCM (10 mL), followed by addition of Et$_3$N (303 mg, 3.0 mmol, 2.0 eq.). The mixture was stirred for 12 h under nitrogen, and then concentrated under reduced pressure. The residual material was purified by flash column chromatography (silica-gel; eluent: PE:EA, 5:1), giving (9H-fluoren-9-yl)methyl 4-(4-(2,6-dichlorobenzamido)-1-dodecanoyl-1H-pyrazole-3-carboxamido)piperidine-1-carboxylate (800 mg, 68%). (9H-Fluoren-9-yl)methyl 4-(4-(2,6-dichlorobenzamido)-1-dodecanoyl-1H-pyrazole-3-carboxamido)piperidine-1-carboxylate (560 mg, 0.71 mmol, 1.0 eq.) was dissolved in DMF (5 mL), and treated with DIPEA (5 mL). The mixture was stirred for 48 h, and then concentrated under reduced pressure. The residual material was purified by flash column chromatography (silica-gel; eluent: PE:EA, 2:1), affording compound 27 (150 mg, 68%): $^1$H NMR (CD$_3$OD, 500 MHz) δ ppm 0.89-1.01 (m, 3H), 1.30 (s, 17H), 1.50-1.61 (m, 3H), 1.96 (d, J=10 Hz, 2H), 2.40 (s, 2H), 2.80 (t, J=15 Hz, 1H), 3.21 (t, J=15 Hz, 1H), 3.98 (t, J=15 Hz, 1H), 4.10 (s, 1H), 4.50 (d, J=10 Hz, 1H), 7.46-7.51 (m, 3H), 8.36 (s, 1H); $^{13}$C NMR (CD$_3$OD, 125 MHz) δ ppm 14.38, 23.67, 26.64, 30.40, 30.44, 30.48, 30.58, 30.68, 32.39, 33.02, 33.28, 34.12, 41.87, 45.87, 47.63, 122.35, 123.02, 129.48, 132.76, 133.47, 134.53, 136.69, 163.26, 164.81, 174.11; m/z (ESI$^+$) 564.0 (M+H).

Example 19: Preparation of ((4-(4-(2,6-dichlorobenzamido)-1-dodecanoyl-1H-pyrazole-3-carboxamido)piperidin-1-yl)(phenoxy)phosphinyl)-L-alanine methyl Ester (Compound 38)

Compound 12 (310 mg, 0.5 mmol, 1.0 eq.) and dodecanoyl chloride (130 mg, 0.6 mmol, 1.2 eq.) were dissolved in DCM (5 mL), followed by addition of Et$_3$N (101 mg, 1.0 mmol, 2.0 eq.). The mixture was stirred for 12 h under nitrogen, and then concentrated under reduced pressure. The residual material was purified by flash column chromatography (silica-gel; eluent: PE:EA, 3:1), affording compound 38 (120 mg, 30%): $^1$H NMR (CD$_3$OD, 500 MHz) δ ppm 0.92 (s, 3H), 1.32-1.45 (m, 21H), 1.61 (s, 2H), 1.78-1.90 (m, 4H), 2.84 (s, 2H), 3.23 (s, 2H), 3.73 (s, 4H), 3.96 (s, 1H), 7.18-7.24 (m, 3H), 7.37 (s, 2H), 7.50 (s, 3H), 8.93 (s, 1H); $^{13}$C NMR (CD$_3$OD, 125 MHz) δ ppm 14.46, 20.68, 23.68, 25.19, 30.08, 30.41, 30.56, 30.67, 32.85, 33.00, 34.12, 45.00, 45.21, 48.22, 50.98, 52.72, 120.46, 121.41, 121.57, 125.23, 125.67, 129.49, 130.64, 132.91, 133.30, 136.21, 138.79, 152.46, 163.30, 163.46; $^{31}$P NMR (CD$_3$OD, 203 MHz) δ ppm 10.54, 11.09; m/z (ESI$^+$) 805.2 (M+H).

Example 20: Synthesis of 4-(4-(2,6-dichlorobenzamido)-1H-pyrazole-3-carboxamido)piperidine-1-acetic acid hydrobromide (Compound 54)

To a stirred solution of 4-(2,6-dichlorobenzamido)-N-(piperidin-4-yl)-1H-pyrazole-3-carboxamide hydrochloride (900 mg, 2.1 mmol, 1.0 eq.) and Triethylamine (530 mg, 5.3 mmol, 2.5 eq.) in DCM (25 mL) was added, dropwise under nitrogen, tert-butyl 2-bromoacetate (419 mg, 2.1 mmol, 1.0 eq.). The reaction mixture was stirred overnight at room temperature. The solvent was removed under reduced pressure and the residue was purified by flash column chromatography (silica-gel; eluent: DCM:MeOH, 20:1), affording tert-butyl 4-(4-(2,6-dichlorobenzamido)-1H-pyrazole-3-carboxamido)piperidine-1-acetate (620 mg, 59.5%): $^1$H NMR (500 MHz, CD$_3$OD) δ ppm 1.46 (s, 9H), 1.70 (d, J=10.9 Hz, 2H), 1.89 (d, J=11.7 Hz, 2H), 2.30 (t, J=11.5 Hz, 2H), 2.94 (d, J=10.4 Hz, 2H), 3.13 (s, 2H), 3.84 (s, 1H), 7.47 (dd, J=16.4, 6.6 Hz, 3H), 8.33 (s, 1H). To a stirred solution of this acetate derivative (620 mg, 1.2 mmol, 1.0 eq.) in anhydrous DCM (16 mL) was added TFA (8 mL). The reaction mixture was stirred overnight at room temperature. Solvent was removed under reduced pressure and the residue was treated with 40% HBr (5 mL) and lyophilized, giving compound 54 (533 mg, 85.2%): $^1$H NMR (500 MHz, D$_2$O) δ ppm 2.04 (d, J=13.2 Hz, 2H), 2.32 (d, J=13.4 Hz, 2H), 3.30 (t, J=12.3 Hz, 2H), 3.82 (d, J=11.9 Hz, 2H), 4.13 (d, J=28.8 Hz, 3H), 7.54 (d, J=6.5 Hz, 1H), 7.56 (s, 2H), 8.40 (s, 1H); $^{13}$C NMR (125 MHz, DMSO-d$_6$) δ ppm 28.42, 43.94, 51.85, 55.33, 121.65, 128.55, 131.35, 132.06, 132.39, 135.42, 160.59, 162.85, 167.21; m/z (ESI$^+$) 439.8 (M+H).

Example 21: Toxicity Study in Mice

Male mice (BABL/c) of 20 to 22 g were maintained under standard conditions and randomized into groups. On day 1, three groups of animals were administered intravenously AT7519 (methanesulfonate salt form), compound 11, and compound 12, respectively. Doses were calculated and expressed in mmol/kg-body weight, and drug tolerability, pharmacokinetics, and body weight effect were assessed.

(a) Tolerability: Sixty animals were divided into 3 groups (20 each group), and dosed with each test compound: AT7519, 0.031 mmol/kg (an equivalent to 12 mg/kg of AT7519 free form); compound 11, 0.062 mmol/kg; compound 12, 0.124 mmol/kg, respectively. Another group of animals (5 in the group) were given AT7519 at a dose of 0.039 mmol/kg (15 mg/kg) as reference. The results are summarized in Table 2.

TABLE 2

Animal death after i.v.-administration of different compounds

| Compound | AT7519 | | Compound 11 | Compound 12 |
|---|---|---|---|---|
| Dose (mmol/kg) | 0.031 | 0.039 | 0.062 | 0.124 |
| Animals in group | 20 | 5 | 20 | 20 |
| Number of deaths | 4 | 5 | 0 | 0 |
| Death rate (%) | 20 | 100 | 0 | 0 |

As indicated by the data in Table 2, the low dose (0.031 mmol/kg) of AT7519 caused animal death rate of 20%, while the high dose (0.039 mmol/kg) of AT7519 killed all the animals in the group even though the dose was only increased by 25% (from the low dose), indicating that 0.031 mmol/kg was a threshold lethal dose of AT7519. In contrast, compounds 11 and 12 did not cause a single death even if the compounds were dosed at a level of 2-fold and 4-fold of molar-equivalents to the AT7519 threshold level. In summary, compounds 11 and 12 were much less toxic than AT7519.

(b) Toxicokinetics: In order to confirm the validity of the above tox-study, plasma AT7519 concentration after administration of each compound was determined. The i.v. doses of AT7519, compound 11, and compound 12 were the same as above, namely 0.031 mmol/kg, 0.062 mmol/kg, and 0.124 mmol/kg, respectively. Blood samples were collected at 2 min, 10 min, 1 h, and 4 h. Concentration of T7519 was analyzed in each sample using LC-MS/MS method. The results are summarized in Table 3, and the concentration-time curves are illustrated in FIG. 1.

TABLE 3

Concentration* of AT7519 in plasma of mice from toxicokinetics study

| Compound | AT7519 | Compound 11 | Compound 12 |
|---|---|---|---|
| Dose (mmol/kg) | 0.031 | 0.062 | 0.124 |
| Dosing route | I.V. | I.V. | I.V. |
| Dosing Conc. (mM) | 0.0031 | 0.0062 | 0.0124 |
| Dosing volume (mL/kg) | 10 | 10 | 10 |
| 2 min | 10230 | 45000 | 99067 |
| 10 min | 1837 | 12627 | 17867 |
| 1 h | 489 | 970 | 1657 |
| 4 h | 47 | 170 | 197 |

*The concentration is in ng/mL.

The data in Table 3 show that both compounds 11 and 12 were converted to AT7519 within a very short time (<2 min) after intravenous injection. For each time point, there was a rough correlation between the plasma concentration and the dose, regardless of whether the compound administered was AT7519 itself or its prodrugs (Compound 11, or Compound 12). In the cases of Compounds 11 and 12, the plasma AT7519 exposures were much higher.

(c) Drug effect on animal body weight after a single dose intravenously: Sixty animals were divided into 3 groups (20 in each group), and on day 0 (the initial day of the study) dosed with each test compound: AT7519, 0.031 mmol/kg (an equivalent to 12 mg/kg of AT7519 free form); compound 11, 0.062 mmol/kg; or compound 12, 0.124 mmol/kg, respectively. Clinical observations were made in the following schedule: continuous observation in the first four hours after dosing, and then twice daily, at one week time, and at day 14. The parameters for observation included animal's physical and mental behaviors, autonomous activity, hair, gland secretion, feces, and death. Body temperature was taken at pre-dosing, and on days 3, 5, 7, and 10 post-dosing.

In the study, 4 animals died in the AT7519 group, and no animal death was observed in groups dosed with compounds 11 and 12.

Figure 2:
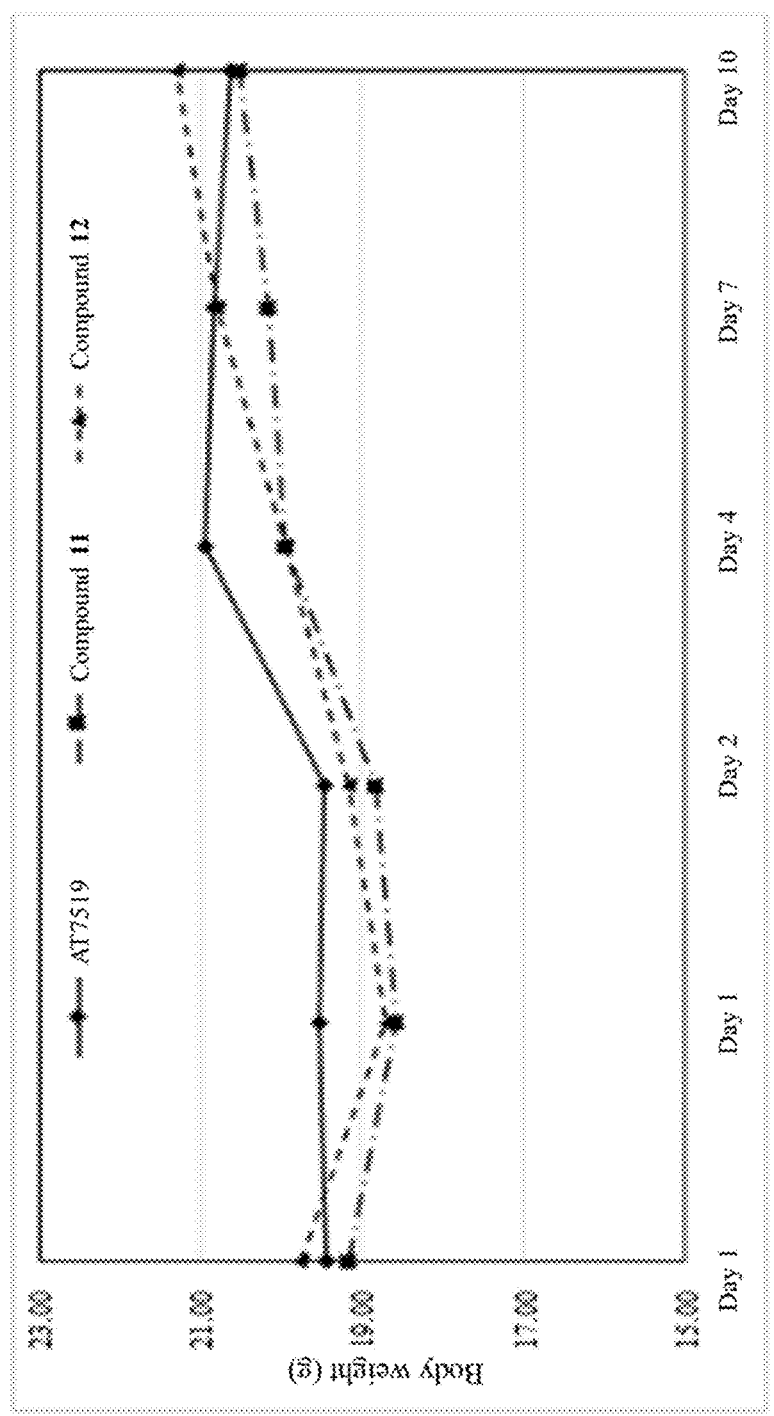
FIG. 2 shows body-weight changes with time after intravenous administration of AT7519, compound 11, and compound 12 to mice.

The body weights of the animals are summarized in Table 4, and the trend lines for animal body weight changes in each group are given in FIG. 2. The body weight was average weight of all the animals in the group from a single measurement.

TABLE 4

Animal body-weight changes after dosing

| | Body weight (g) | | | | | |
|---|---|---|---|---|---|---|
| Compound | Day 0 | Day 1 | Day 2 | Day 4 | Day 7 | Day 10 |
| AT7519 | 19.44 | 19.53 | 19.45 | 20.94 | 20.83 | 20.63 |
| 11 | 19.16 | 18.58 | 18.83 | 19.95 | 20.16 | 20.52 |
| 12 | 19.75 | 18.70 | 19.17 | 19.95 | 20.79 | 21.30 |

The results indicated that during the first few days, the body weights for animals receiving high doses of compounds (compounds 11 and 12) had a trend of decrease but within a narrow range, i.e., 3 to 5% in comparison to that receiving AT7519. On day 7 and afterwards, body weights of animals were the same or very similar across all groups. It was postulated that the initial body weight decrease was due to the normal reaction of the animals to a very high dose of compounds given to the animals.

Example 22: Toxicokinetic Study in Rats

Male SD (Sprague Dawley) rats of body weight 220 to 240 g were maintained under standard conditions and randomized into three groups. On day 0 (initial day), all the animals were given one of the three compounds intravenously. Dose was calculated in mmol/kg.

(a) Dose exploration: One animal from each group was given the preset high dose of each compound. Observations are given in Table 5.

TABLE 5

Toxicity of the test compounds

| Compound | Animal No. | Body weight (g) | Dose (mmol/kg) | Animal death |
|---|---|---|---|---|
| AT7519 | 1 | 244 | 0.049 | Died immediately post-dosing |
| 11 | 7 | 233 | 0.055 | Died at 2 min post-dosing |
| 12 | 13 | 237 | 0.125 | Behaved normally |

The data in Table 5 showed that only compound 12 did not induce the animal death while both AT7519 and compound 11 were already at their lethal doses (doses are shown in the table).

Figure 3:
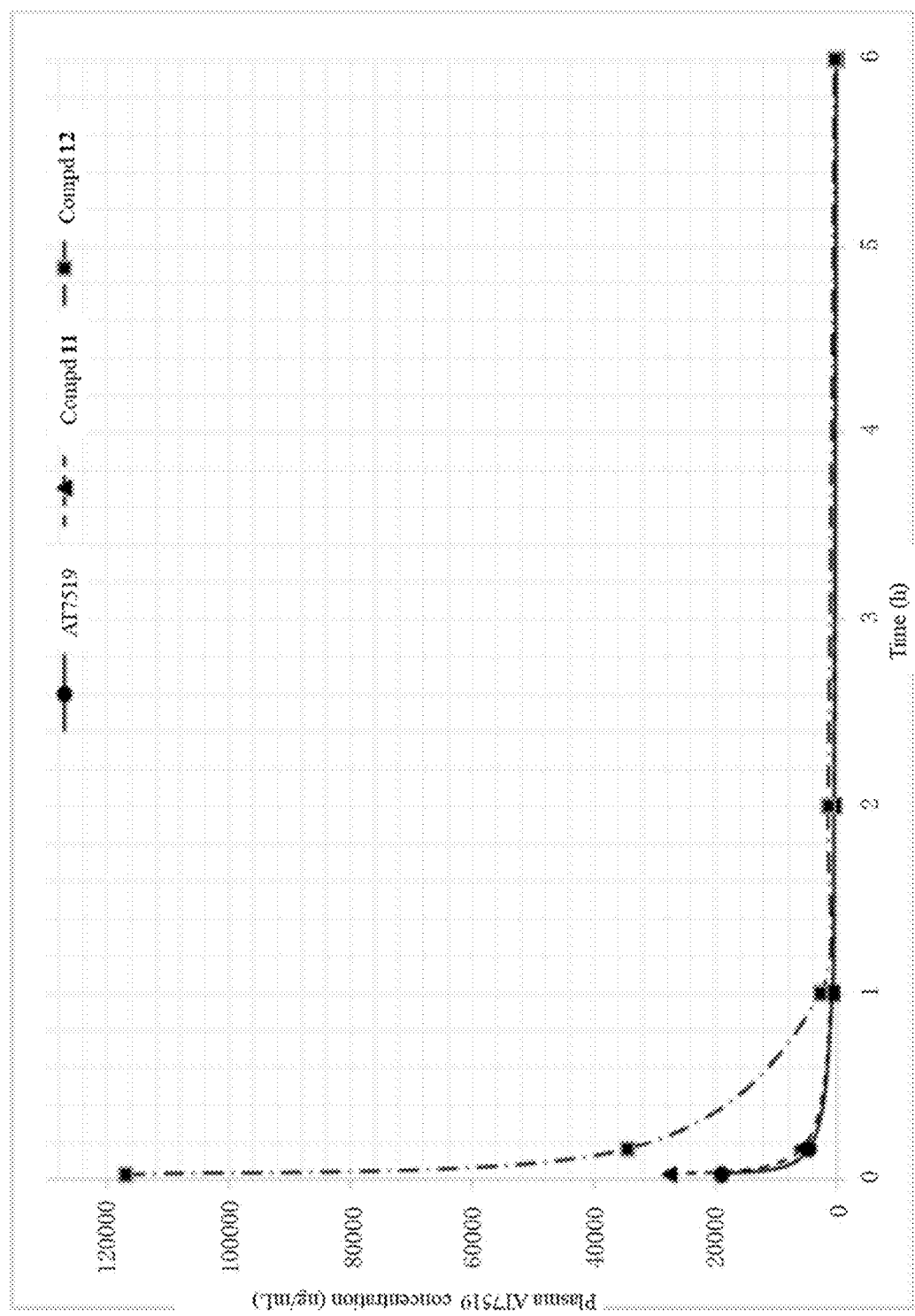
FIG. 3 shows plasma AT7519 concentration-time curves after intravenous administration of AT7519, compound 11, and compound 12 at molar-equivalent dose to rats.

(b) TK study: The remaining animals were randomized into three groups, with 6 in each group. At time 0, animals were administered either AT7519 (dose, 0.039 mmol/kg), or compound 11 (0.050 mmol/kg), or compound 12 (0.124 mmol/kg). TK analysis was conducted as follows: Blood samples were collected at time points of 2 min, 10 min, 1 h, 2 h, and 6 h into sample tube (heparinized). After converting to plasma samples, AT7519 concentration was analyzed (LC-MS/MS). The results are summarized in Table 6, and the concentration-time curves are given in FIG. 3.

TABLE 6

Plasma AT7519 concentration in rat TK study

| Compound | AT7519 | 11 | 12 |
|---|---|---|---|
| Dose (mmol/kg) | 0.039 | 0.050 | 0.124 |
| Dosing route | I.V. | I.V. | I.V. |
| Solution Conc. (mM) | 0.0039 | 0.0050 | 0.0125 |
| Dosing Volume (mL/kg) | 10 | 10 | 10 |
| Time | AT7519 concentration (ng/mL) | | |
| 2 min | 19125 | 27680 | 117000 |
| 10 min | 4600 | 5896 | 34400 |
| 1 h | 814 | 891 | 2798 |
| 4 h | 554 | 601 | 1530 |
| 6 h | 148 | 159 | 449 |

Example 23: Toxicity Study in Rats

Male SD (Sprague Dawley) rats were dosed intravenously with 0.031 mmol-equivalent/kg of each test compound, with the injection time controlled between 30 to 45 seconds. A four-level score system was applied to describe the toxicity of the test compound: A, animal died during the injection; B, animal experienced shock within 5 minutes after intravenous administration, and falling to the ground and decreasing activity after recovery; C, no animal death but falling to the ground within 30 min with decreasing activity; D, no animal death, no obvious abnormal behavior, and no obvious body-weight decrease. For the results from selected compounds, see Table 7.

TABLE 7

Toxicity scores in rats

| Compound | Toxicity Score |
|---|---|
| AT7519 | B |
| 2 | C |
| 3 | D |
| 4 | D |
| 5 | C |
| 6 | C |
| 7 | D |
| 8 | C |
| 10 | C |
| 11 | D |
| 12 | D |
| 13 | C |
| 16 | D |
| 17 | B |
| 18 | D |
| 20 | B |
| 25 | A |
| 27 | C |
| 38 | D |
| 54 | D |

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A compound which is:

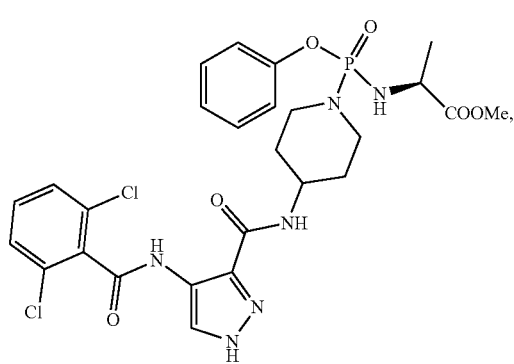 [SMILES: COC(=O)[C@H](C)NP(=O)(Oc1ccccc1)N1CCC(NC(=O)c2n[nH]cc2NC(=O)c2c(Cl)cccc2Cl)CC1]

or a pharmaceutically acceptable salt or ester thereof.

2. The compound of claim 1, wherein the compound is:

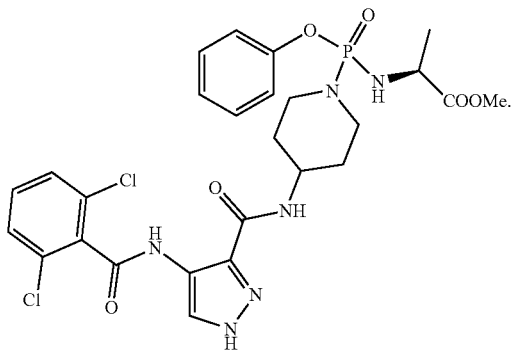 [SMILES: COC(=O)[C@H](C)NP(=O)(Oc1ccccc1)N1CCC(NC(=O)c2n[nH]cc2NC(=O)c2c(Cl)cccc2Cl)CC1]

3. A pharmaceutical composition comprising the compound of claim 1 and a pharmaceutically acceptable carrier.

4. The pharmaceutical composition of claim 3, wherein the composition is suitable for oral administration.

5. The pharmaceutical composition of claim 4, wherein the composition is in the form of a hard shell gelatin capsule, a soft shell gelatin capsule, a cachet, a pill, a tablet, a lozenge, a powder, a granule, a pellet, a solution, a pastille, a dragee, an emulsion, an elixir, or a syrup.

6. The pharmaceutical composition of claim 3, wherein the composition is injectable.

7. The pharmaceutical composition of claim 6, wherein the composition is suitable for intravenous, intramuscular, intraperitoneal, or subcutaneous administration.

8. A method for the inhibition or modulation of a cyclin dependent kinase (CDK) and/or glycogen synthase kinase-3 (GSK-3) in a subject, comprising administering to the subject an effective amount of the compound of claim 1, such that the CDK and/or GSK-3 is inhibited or modulated in the subject.

9. The method of claim 8, wherein the subject suffers from a disease state or condition mediated by CDK and/or GSK-3.

10. The method of claim 9, wherein the disease state or condition is a tumor or a cancer.

11. A method for treating a disease state or condition mediated by a cyclin dependent kinase (CDK) and/or glycogen synthase kinase-3 (GSK-3) in a subject, comprising administering to the subject an effective amount of the compound of claim 1 or a pharmaceutically acceptable salt or ester thereof, such that the disease state or condition is treated in the subject.

12. The method of claim 11, wherein CDK and/or GSK-3 is inhibited or modulated in the subject.

13. The method of claim 11, wherein the disease state or condition is a tumor or a cancer.

14. A method for treating a tumor or a cancer in a subject, comprising administering to the subject an effective amount of the compound of claim 1 or a pharmaceutically acceptable salt or ester thereof, such that the tumor or the cancer is treated in the subject.

15. The method of claim 14, wherein the tumor or cancer is selected from multiple myeloma (MM), chronic lymphocytic leukemia (CLL), acute myeloid leukema (AML), mantle cell lymphoma (MCL), solid tumors, refractory solid tumors, non-Hodgkin lymphoma, hematological neoplasm, neuroblastoma, colorectal cancer, cervical cancer, lung cancer, leukemia, breast cancer, pancreatic cancer, B-cell malignancy, neoplasm, metastatic tumor, carcinoma of the colon, and myelodysplastic syndrome.

16. The method of claim 14, wherein the effective amount is an amount effective to inhibit abnormal cell growth.

17. The method of claim 14, wherein the subject is a mammal.

18. The method of claim 17, wherein the mammal is a human.

19. The method of claim 14, wherein said administering comprises intravenous, intramuscular, intraperitoneal, or subcutaneous administration.

20. The method of claim 14, wherein said administering comprises oral administration.

\* \* \* \* \*